United States Patent

Ouchi

[11] Patent Number: 5,904,647
[45] Date of Patent: May 18, 1999

[54] TREATMENT ACCESSORIES FOR AN ENDOSCOPE

[75] Inventor: Teruo Ouchi, Tokyo, Japan

[73] Assignee: Asahi Kogyo Kabushiki Kaisha, Tokyo, Japan

[21] Appl. No.: 08/832,817

[22] Filed: Apr. 4, 1997

[30] Foreign Application Priority Data

| Oct. 8, 1996 | [JP] | Japan | ................................. 8-267186 |
| Jan. 13, 1997 | [JP] | Japan | ................................. 9-003440 |
| Feb. 5, 1997 | [JP] | Japan | ................................. 9-022268 |

[51] Int. Cl.$^6$ ........................................................ A61B 1/00
[52] U.S. Cl. ........................................... 600/104; 606/206
[58] Field of Search ................................. 600/104, 106, 600/210, 217; 606/205, 206, 207, 208

[56] References Cited

U.S. PATENT DOCUMENTS

| 4,108,162 | 8/1978 | Chikashige et al. . |
| 4,271,845 | 6/1981 | Chikashige et al. . |
| 4,351,323 | 9/1982 | Ouchi et al. . |
| 4,982,727 | 1/1991 | Sato . |
| 5,624,379 | 4/1997 | Ganz et al. .............................. 600/104 |

FOREIGN PATENT DOCUMENTS

| 48-28751 | 9/1973 | Japan . |
| 52-22146 | 5/1977 | Japan . |
| 53-150092 | 11/1978 | Japan . |
| 56-40424 | 9/1981 | Japan . |
| 1119621 | 8/1989 | Japan . |
| 3-37605 | 8/1991 | Japan . |

OTHER PUBLICATIONS

"Gastrointestinal Endoscopy", Martin B. Grossman, M.D., *Clinical Symposia*, vol. 32, No. 3, CIBA Pharmaceutical Company, Summit, New Jersey, 1980.

An English Translation of JP Patent No. 48–28751.

*Primary Examiner*—Beverly M. Flanagan
*Attorney, Agent, or Firm*—Greenblum & Bernstein, P.L.C.

[57] ABSTRACT

A treatment apparatus for use with an endoscope, by being inserted in a forceps channel of the endoscope, includes an elongated flexible element connected, at a distal end thereof, to a treatment instrument. In particular, the flexible element includes at least two bendable portions. A first bendable portion has a predetermined flexibility and a second bendable portion has a greater flexibility and is shorter than the first bendable portion. The second bendable portion is located between the first bendable portion and the treatment instrument and at least a portion of the first bendable portion and the entire second bendable portion protrude from a distal end of the forceps channel when the treatment instrument is in use.

28 Claims, 42 Drawing Sheets ered to make the second bendable portion more flexible in the one direction.
TREATMENT ACCESSORIES FOR AN ENDOSCOPE

BACKGROUND OF THE INVENTION

The present invention relates to a treatment accessory having a flexible shaft which is slidably inserted in a forceps channel of an endoscope.

Generally, the flexible shaft of a treatment accessory for an endoscope is formed as a closely wound stainless-steel coil. A variety of types of treatment accessories are formed by securing different treating devices, such as forceps or the like, to the distal end of the flexible shaft.

As shown in FIG. 10, when a conventional treatment accessory (in this case), a forceps as a treating device is used to treat an affected part A of human tissue, the distal end of the flexible shaft 91 is extended from a forceps channel 93 of an endoscope 92 straight towards the affected part A. In this example, since the affected part A is not directly in front of the treatment accessory, it is difficult to treat the affected part A accurately.

In this case, it may be necessary to press contact the distal end of the treatment accessory, i.e., attempt to hook the treatment accessory onto the tissue in the neighborhood of the affected part A, and then further extend the flexible shaft 91 from the forceps channel 93, such that the flexible shaft 91 is bent and the orientation of the distal end of the treatment accessory is changed. However, since the flexible shaft 91 of the treatment accessory is a closely wound coil having a relatively strong elasticity, the distal end of the treatment accessory may slip off the portion at which it has been press contacted or hooked. If the distal end slips, the flexible shaft 91 elastically straightens back to the position shown in FIG. 10.

In order to overcome the above problem, treatment accessories having a flexible shaft which is remotely controlled to bend in a desired direction are known. Examples of such an instrument are disclosed in Japanese Utility Model Registration Publication SHO 52-22146, Japan Utility Model Provisional Publication HEI 1-119621, and the like.

In such an instrument, however, a manipulation portion of the endoscope must include mechanisms for simultaneously performing the bending operation and the treatment of the affected portion A. Such a device is difficult for a user to operate since the positioning of the distal end of the treatment accessory in front of the affected part is difficult. Further, in such an instrument, both an operation wire for the operation of the treating device of the affected part and another operation wire for the bending of the flexible shaft are enclosed within the flexible shaft. As such, the flexible shaft must be larger and more rigid, making it more difficult to insert the flexible shaft in the forceps channel of the endoscope and then bend the flexible shaft at the appropriate position.

In a particular case, the treating device may be a cutting or grasping device that opens and closes, such as a biopsy forceps, a grasping forceps or the like, which includes a plurality of members that are openable about a fulcrum to be used for collecting or grasping material, such as mucous or the like, inside a living body. In this case, generally, the end of such a treating device is formed to be substantially spherical in a closed state so that the device can be inserted in channels within the body easily, and in order to prevent the device from damaging the inner wall of the body.

A conventional treating device generally has a shape as shown in FIG. 34. The conventional treating device includes two cups 94 that can be opened and closed. When such a conventional treating device is pressed against an affected part A from other than a vertical direction, for example, diagonally as shown in FIG. 34, the spherical surface of the cup 94 may slip on the tissue surface, such that the material in the affected portion A cannot be collected easily.

In order to overcome the problem of slipping, a treatment device, as disclosed in Japanese Utility Model Publication-SHO 56-40424, and as shown in example form in FIG. 35, may be provided with cups 94' having an extended end portion 95. With this arrangement of a treating device, the extended end portion 95 catches on and enters into the tissue such that the cup 94' does not slip and the position of the treatment device may be more easily adjusted with respect to the affected part A.

However, as shown in FIG. 35, the provision of the extended end portion 95 may cause a problem in that, when the opened cups 94' are closed, the tissue surface is pushed away from the cups 94' such that it is difficult to collect a large amount of material.

SUMMARY OF THE INVENTION

It is therefore an object of the present invention to provide an improved treatment accessory for an endoscope which is easy to insert in a forceps channel and which allows easy adjustment of the position of a distal end of the treatment accessory in relation to an affected part with a simple structure.

It is another object of the present invention to provide an improved treatment accessory for an endoscope with which treatment of the affected portion can be achieved appropriately even if the distal end of the treatment accessory approaches the affected part at an oblique angle.

According to a first aspect of the invention, there is provided a treatment apparatus for use with an endoscope, by being inserted in a forceps channel of the endoscope, that includes an elongated flexible element connected, at a distal end thereof, to a treatment instrument. In particular, the flexible element includes at least two bendable portions. A first bendable portion has a predetermined flexibility and a second bendable portion has a greater flexibility and is shorter than the first bendable portion. The second bendable portion is located between the first bendable portion and the treatment instrument and at least a portion of the first bendable portion and the entire second bendable portion protrude from a distal end of the forceps channel when the treatment instrument is in use.

The provision of the second bendable portion allows the flexible element to be bent more easily in order to adjust the position of the treatment instrument with respect to an affected part.

In a preferred embodiment, the second bendable portion is more flexible than the first bendable portion in one direction.

In a particular case, the treatment instrument may be a forceps having jaws which open in a predetermined direction that is the same as the one direction. Alternatively, the jaws may open in a predetermined direction that is perpendicular to the one direction.

In another preferred embodiment, the second bendable portion includes a plurality of pivotally connected annular pipe portions. In this embodiment, the second bendable portion may be bendable in any direction.

In yet another preferred embodiment, the second bendable portion includes a flexible cylindrical member having cut-out portions.

In yet another preferred embodiment, the second bendable portion includes a metal coil embedded in a cylindrical elastic material.

In this aspect of the invention, the bending angle of the second bendable portion is preferably less than 70 degrees and the length of the second bendable portion is preferably equal to or less than 50 mm.

In yet another preferred embodiment, the first and second bendable portions include wound coils, the coils of the second bendable portion being more loosely wound than the first bendable portion.

In yet another preferred embodiment, the first and second bendable portions include flexible sheaths, and a mesh material being embedded in only the first bendable portion.

In yet another preferred embodiment, the first and second bendable portions are formed of different materials.

According to another aspect of the invention, there is provided a treatment apparatus for use with an endoscope that has a bendable portion at a distal end thereof. In use, the treatment apparatus is inserted in a forceps channel of the endoscope. In particular, the treatment apparatus includes an elongated flexible element connected, at a distal end thereof, to a treatment instrument. The flexible element includes at least two bendable portions. A first bendable portion has a predetermined flexibility and a second bendable portion is more flexible in one direction than the first bendable portion. The second bendable portion is located between the first bendable portion and the treatment instrument and is located at the bendable portion of the endoscope when inserted in the forceps channel.

Since the second bendable portion is located at the bendable portion of the endoscope and is designed to bend in one direction, the flexible element rotates within the forceps channel to easily and appropriately bend in the same direction as the bendable portion of the endoscope when the bendable portion of the endoscope is adjusted. Thus, adjustment of the bendable portion of the endoscope also results in adjustment of the position of the treatment apparatus.

In a preferred embodiment, the first and second bendable portions include wound coils, the coils of the second bendable portion being thinner than the coils of the first bendable portion.

In another preferred embodiment, the treatment apparatus further includes a third bendable portion located between the second bendable portion and the treatment instrument, the third bendable portion being bent at a predetermined angle with respect to the second bendable portion. In a particular case, the third bendable portion is bent in the same direction as the one direction. Alternatively, the third bendable portion may be bent in an opposite direction to the one direction.

According to yet another aspect of the invention, there is provided a treatment apparatus for use with an endoscope by being inserted in a forceps channel of the endoscope. In particular, the treatment apparatus includes a treatment instrument and an elongated flexible element. The treatment instrument is for treating an object to be treated and includes grasping jaws with at least one projection being provided on each of the grasping jaws. The flexible element is connected, at a distal end thereof, to the treatment instrument and includes a first bendable portion having a predetermined flexibility and a second bendable portion having a greater flexibility than the first bendable portion. The second bendable portion is located between the first bendable portion and the treatment instrument such that when the at least one projection contacts the object to be treated, the second bendable portion bends to position the treatment instrument with respect to the object to be treated.

With the arrangement according to this aspect of the invention, the projection contacts the object to be treated and anchors the treatment instrument so that, as the flexible element is pushed, the second bendable portion bends appropriately, with less risk that the treatment instrument will slide along the object to be treated, even if the treatment instrument approaches the object to be treated at an oblique angle.

In a preferred embodiment, the jaws contact each other at a contact portion when closed, each of the projections being spaced from the contact portion.

In another preferred embodiment, each of the projections is half-ring shaped.

In yet another preferred embodiment, each of the projections is cone-shaped.

In yet another preferred embodiment, the treatment apparatus includes a plurality of projections on each of the jaws.

According to yet another aspect of the invention, there is provided a treatment apparatus for use with an endoscope by being inserted in a forceps channel of the endoscope. The treatment apparatus includes an elongated flexible element and, connected at a distal end of the flexible element, a treatment instrument for treating an object to be treated. The treatment instrument includes grasping jaws, each provided with at least one projection that does not extend beyond a plane perpendicular to a distal end of the grasping jaws whereby when the at least one projection contacts the object to be treated, the flexible element bends to position the treatment instrument with respect to the object to be treated.

Since the projection does not project beyond the distal end of the grasping jaws, the object to be treated is not pushed away from the grasping jaws by the projection when the grasping jaws are being closed to, for example, collect a sample.

DETAILED DESCRIPTION OF THE PREFERRED EMBODIMENTS

Figure 1:
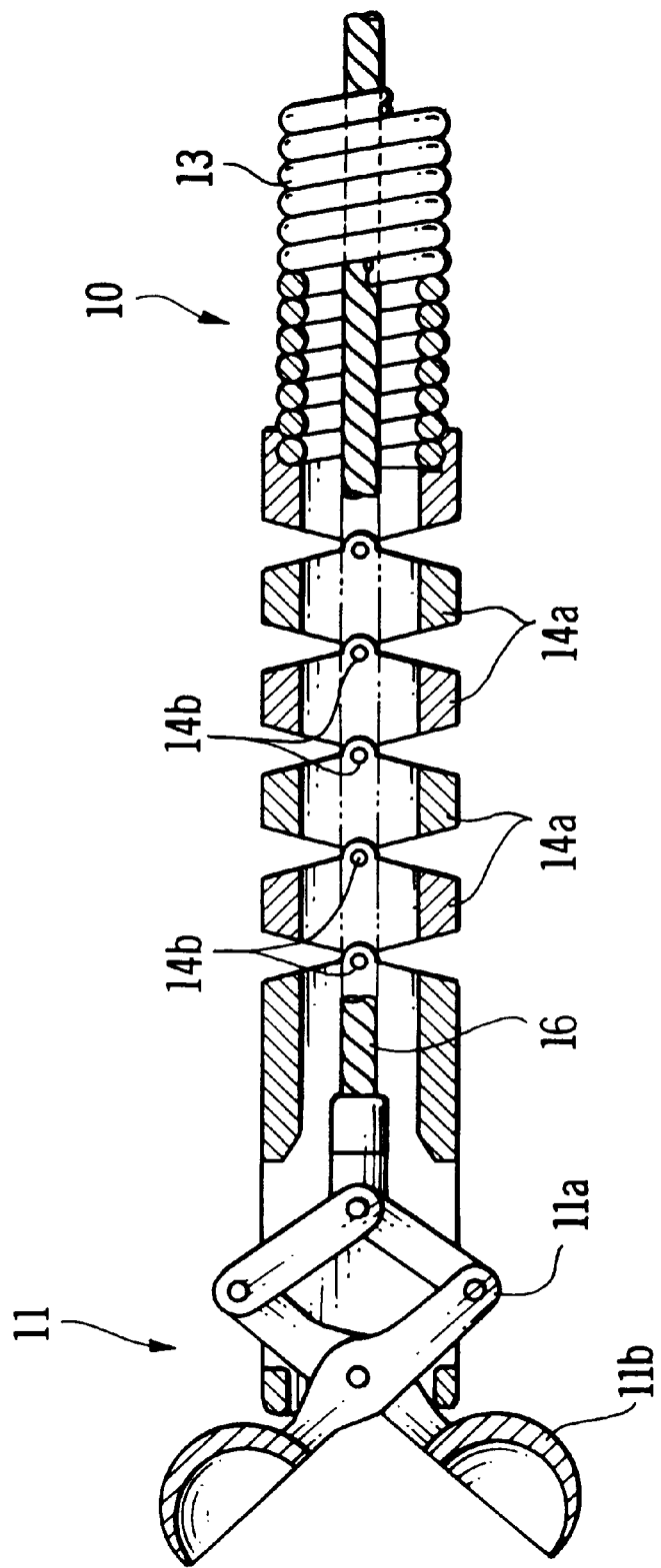
FIG. 1 is a sectional view of a distal end of a treatment accessory according to a first embodiment of the invention.

FIG. 1 shows a distal end of a treatment accessory 10 according to a first embodiment of the invention.

Figure 2:
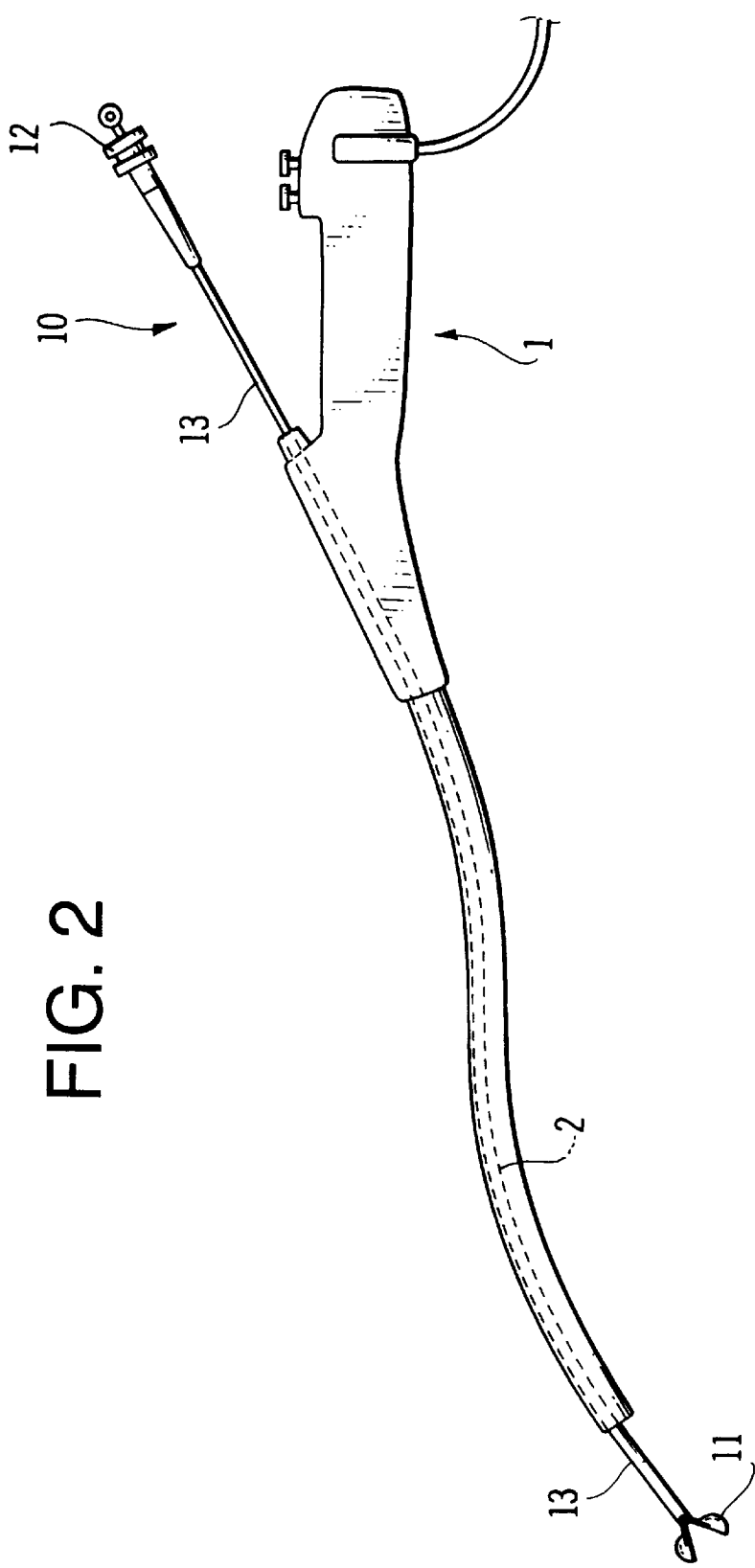
FIG. 2 is a side view of an endoscope having a forceps channel in which the treatment accessory of FIG. 1 is inserted.

As shown in FIG. 2, during use, the treatment accessory 10 is slidably inserted in a forceps channel 2 of an endoscope 1.

The treatment accessory 10 includes a treating device 11, a manipulation portion 12, and a flexible shaft 13 connecting the treating device 11 and the manipulation portion 12. A distal end of the flexible shaft 13 is an end at which the treating device 11 is provided and a proximal end of the flexible shaft 13 is an end at which the manipulation portion is provided. Movement (e.g., opening and/or closing) of the treating device 11 is remotely controlled (manipulated) by the operation of the manipulation portion 12.

The flexible shaft; 13 is, for example, a closely-wound stainless-steel coil having a predetermined diameter substantially throughout the entire length. As shown in FIG. 1, at a distal end portion of the flexible shaft 13, a free-bending portion 14 is provided. The free-bending portion 14 can be bent easily in at least one direction. As an example, the length of the flexible shaft 13 may be from 1 to 2 meters, and the length of the free-bending portion 14 may be from approximately 5 to 30 mm.

In the first embodiment, the treatment accessory 10 that is described is a pair of biopsy forceps. The treating device 11 includes a pair of forceps cups 11b which are opened or closed with a link mechanism 11a. A manipulation wire 16 to drive the link mechanism 11a is slidably enclosed inside the flexible shaft 13 throughout the entire length thereof.

The free-bending portion 14 includes a plurality of stainless-steel pipes 14a rotatably connected with each other. A distal pipe 14a is connected to the treating device 11 and a proximal pipe 14a is connected to the flexible shaft 13. Each pipe 14a is provided with a pair of tongue members that are formed on each of a front end and a rear end of each pipe 14a. The tongue members of adjacent pipes 14a are rotatably connected with a rivet 14b connecting the relevant tongue members. Only the manipulation wire 16 is inserted through the pipes 14a, the flexible shaft 13 is not inserted through the pipes 14a.

As shown in FIG. 1, the distance between the edges of the pipes 14a adjacent to each other is greater at the upper and lower sides in FIG. 1, and smaller at the central portion (i.e., where the tongue portions are riveted together). Accordingly, the free-bending portion 14 can be easily bent, pivoting about the rivets 14b, until the edges of adjacent pipes 14a come into contact. Note that, in this case, the direction of the bending movement coincides with the direction in which the forceps cups 11b open.

The treatment accessory 10 constructed as described above is used as described as follows.

Figure 3:
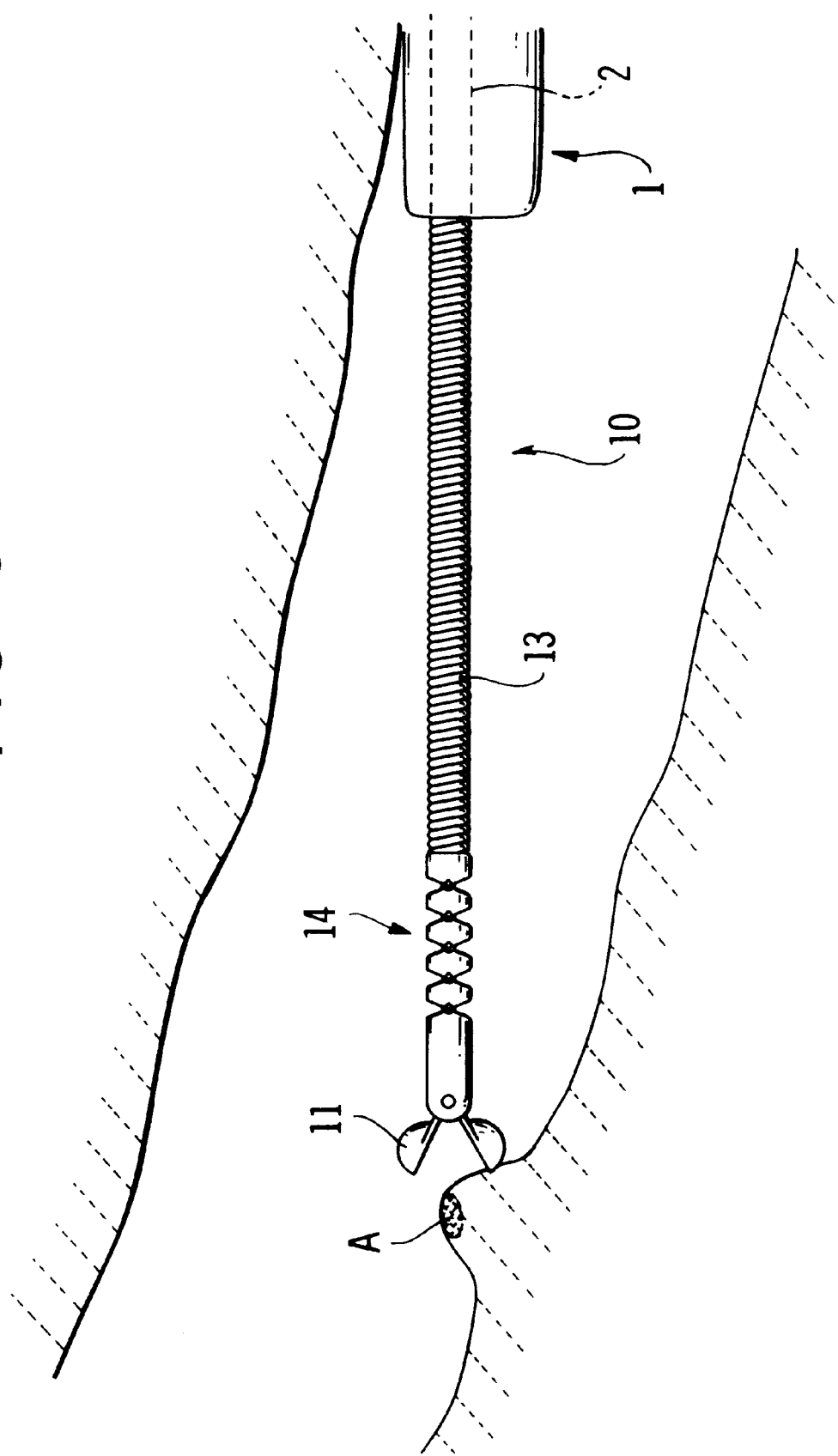
FIG. 3 is a schematic view illustrating the operation of the treatment accessory shown in FIG. 1.

As shown in FIG. 3, the distal end of the treatment accessory 10 is extended from the forceps channel 2 of the endoscope 1, and one of the forceps cups 11b is pressed against a portion of tissue near the affected part A.

Figure 4:
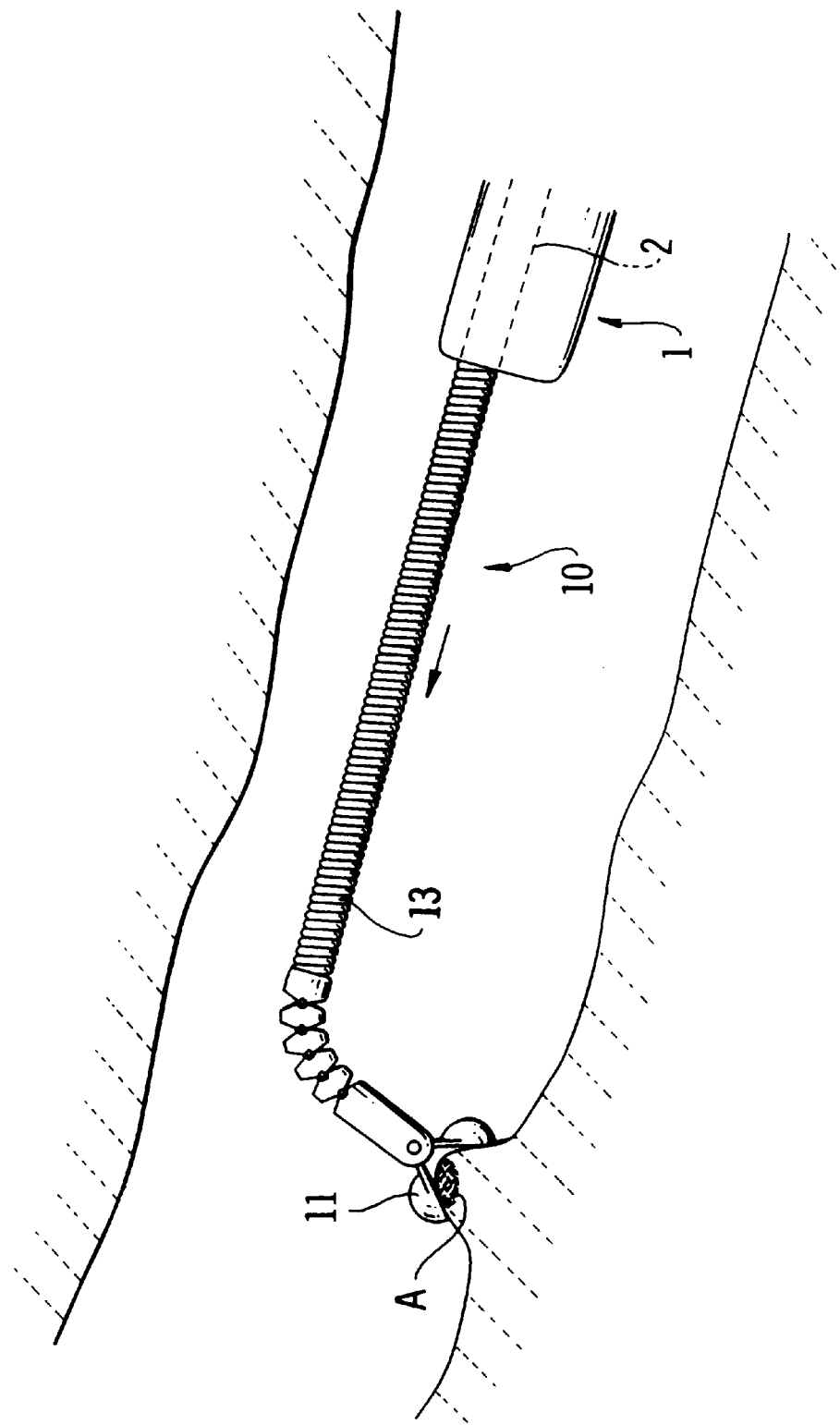
FIG. 4 is a schematic view illustrating the operation of the treatment accessory shown in FIG. 1 in a different state from that shown in FIG. 3.

Then, as shown in FIG. 4, the flexible shaft 13 is further extended from the forceps channel 2 causing the free-bending portion 14 to bend, using the treating device 11, which is pressed against the affected portion as a fulcrum. Thus, the orientation of the treating device 11 changes such that the treating device 11 directly faces the affected part A.

As a result, when, as in this example, the treating device 11 is biopsy forceps, it is easier to collect biopsy tissue from a desired location. If the treating device 11 is a device other than biopsy forceps, the affected part A can be treated appropriately according to its location.

Figure 5:
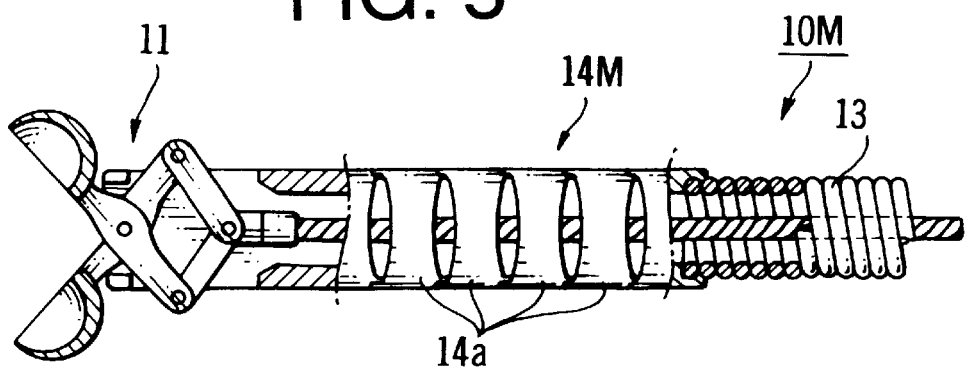
FIG. 5 is a sectional view of a distal end of a treatment accessory according to the first embodiment having an alternative structure.

FIG. 5 shows a modified treatment accessory 10M which is similar to the treatment accessory 10 shown in FIG. 1 except that the modified treatment accessory 10M has a free-bending portion 14M instead of the free-bending portion 14. The free-bending portion 14M bends in a direction perpendicular to the direction in which the treating device 11 opens.

It is noted that the direction where the free-bending portion 14, 14M bends can be set to any direction with reference to the direction in which the treating device 11 opens in order to meet particular requirements of the treatment accessory 10,10M.

Figure 6:
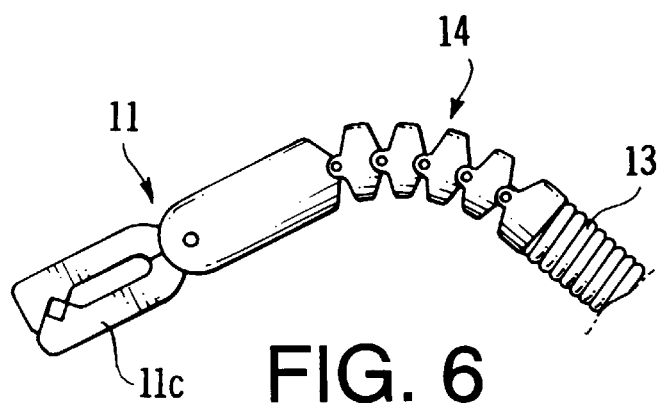
FIG. 6 is a side view of a distal end of a treatment accessory according to the first embodiment having a grasping forceps as a treating device.
Figure 7:
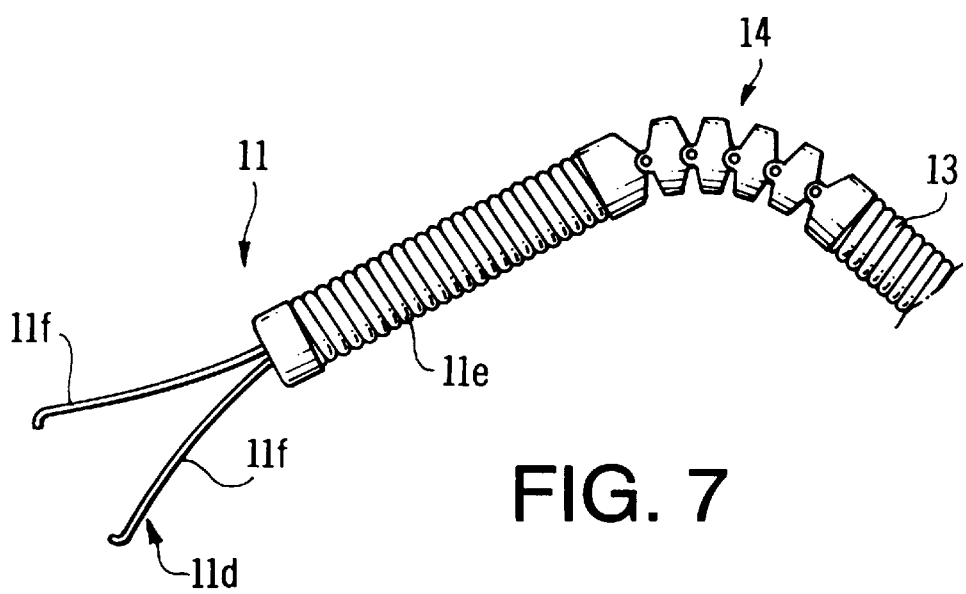
FIG. 7 is a side view of a distal end of a treatment accessory according to the first embodiment having a grasping device as a treating device.

As shown in FIG. 6, the treating device 11 may be a pair of grasping forceps 11c (alligator forceps). Alternatively, as shown in FIG. 7, the treating device 11 may also be a grasping device lid having a pair of flexible wires 11f. In the arrangement shown in FIG. 7, the flexible wires 11f extend from a second flexible coil 11e, and the second flexible coil 11e is connected to the free-bending portion 14. In this case, the flexible wires 11f can be retracted inside the second flexible coil 11e. When the flexible wires 11f are extended from the second flexible coil 11e, the flexible wires 11f open due to elastic force, and when the flexible wires 11f are retracted into the second flexible coil 11e, the flexible wires 11f are closed by contact with the second flexible coil 11e.

Figure 8:
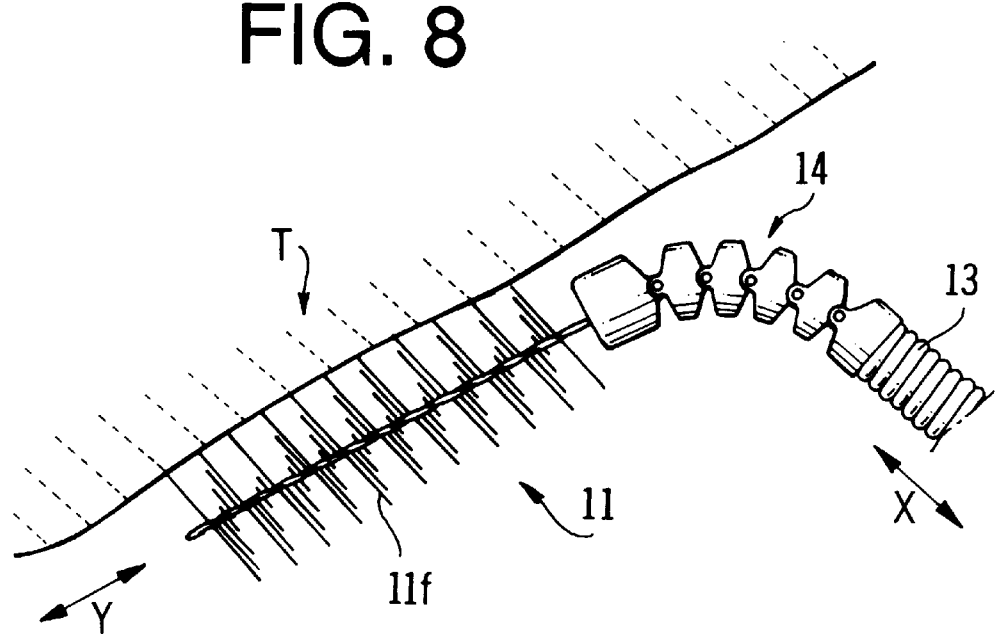
FIG. 8 is a side view of a distal end of a treatment accessory according to the first embodiment having a brush as a treating device.

In FIG. 8, the treating device 11 is a brush 11f, for brushing cytology. By using the free-bending portion 14, even it the flexible shaft 13 cannot be arranged parallel to a tissue surface T, the brush 11f can still be positioned such that, by moving the flexible shaft 13 in relation to the direction in which the flexible shaft extends (i.e., the direction shown by arrow X), the brush 11f moves along the tissue surface T (i.e., the direction shown by arrow Y) to scrape human tissue.

Figure 9:
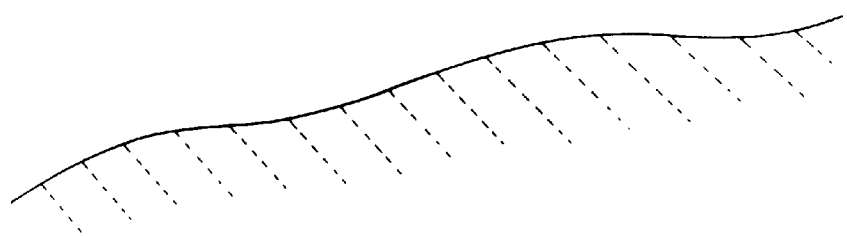
FIG. 9 is a sectional view of a distal end of a treatment accessory according to the first embodiment having another alternative structure.
Figure 10:
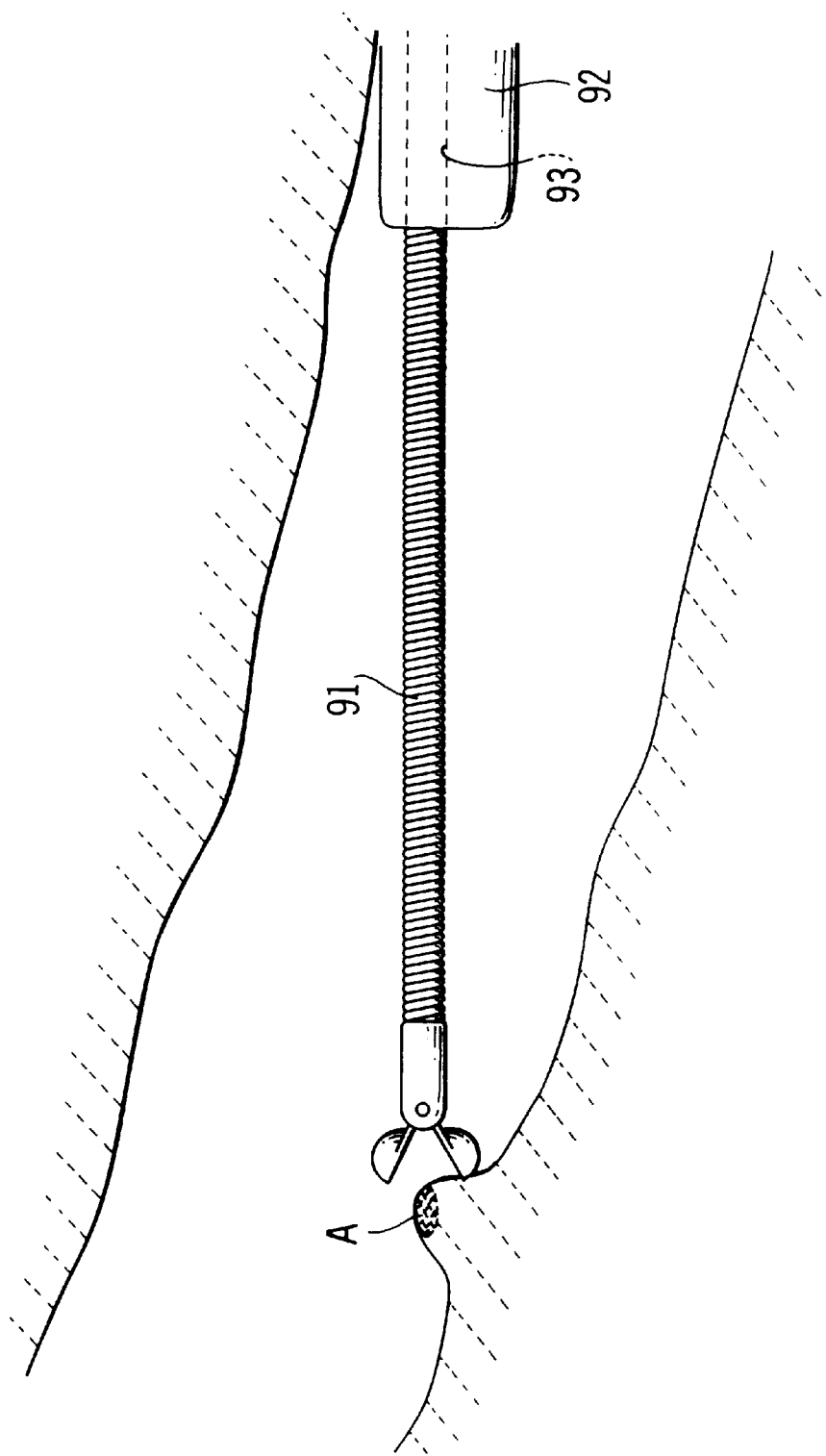
FIG. 10 is a schematic view illustrating the use of a conventional treatment accessory.

The structure of the free-bending portion 14, 14M is not limited to the structure described above. FIG. 9 shows an example of a further alternative free-bending portion 14N. In FIG. 9, a flexible, elastic cylindrical material 14c, such as silicon gum, is provided with V-shape cuts 14d that are alternately formed in opposite directions at opposite sides of the material 14c. The material 14c is also provided with a central opening 14e through which the manipulation wire 16 to drive the treating device 11 may be slidably inserted.

According to the first embodiment, since the treatment accessory 10 is provided with a flexible shaft that is provided with a free-bending portion 14, 14M, 14N at the distal end thereof, the treatment accessory has a simple structure allowing the treating device to be more easily positioned with respect to the affected part A. Further, since the treatment accessory does not require an extra manipulation wire for controlling the curvature of the shaft, the flexible shaft is flexible and small enough to be easily inserted inside the forceps channel 12.

Figure 11:
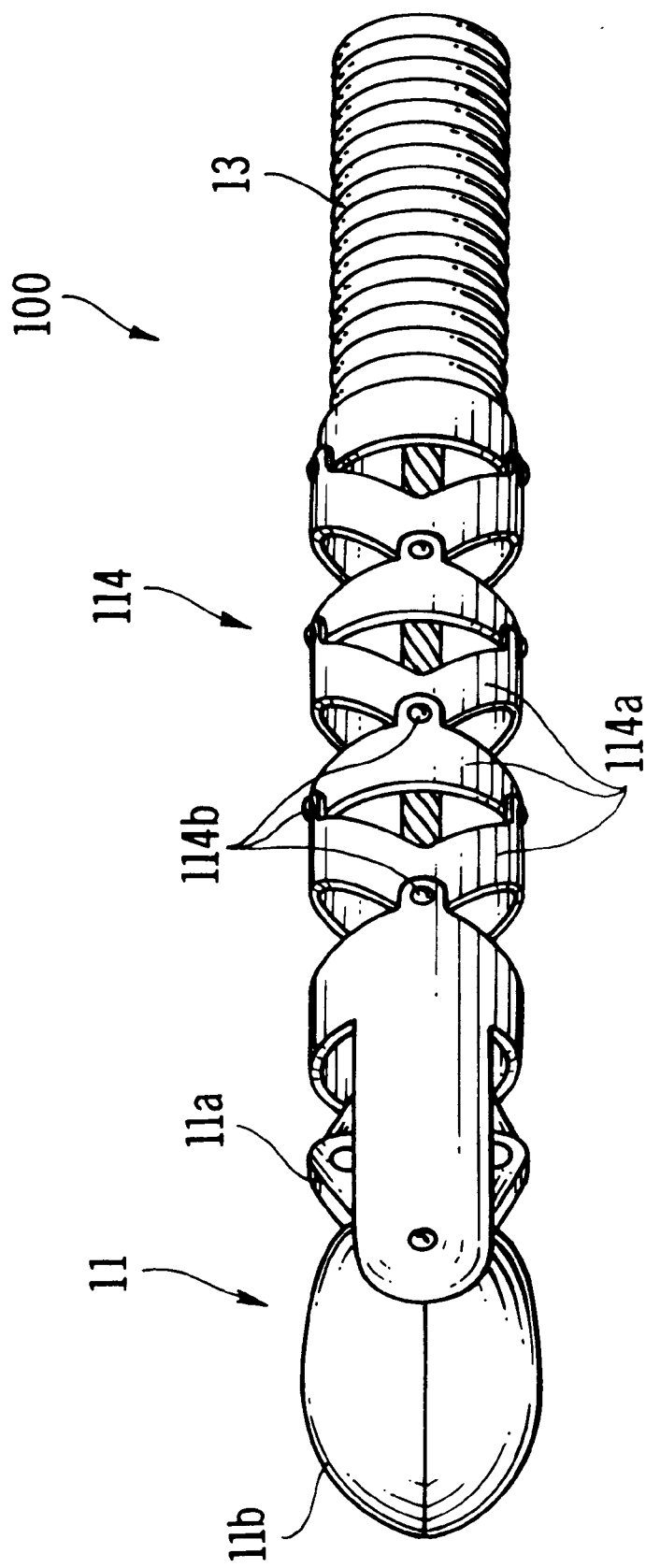
FIG. 11 is a sectional view of a distal end of a treatment accessory according to a second embodiment of the invention.

FIG. 11 shows a treatment accessory 100 according to a second embodiment. The treatment accessory 100 is similar to the treatment accessory 10 of the first embodiment and elements that are the same are given the same reference numbers.

In this embodiment, a free-bending portion 114 includes a plurality of cylindrical joint members 114a which are made from, for example, stainless-steel pipe. Similar to the first embodiment, a distal joint member 114a is connected to the treating device 11 and a proximal joint member 114a is connected to the flexible shaft 13. Each of the joint members 114a is formed, on the front and rear sides thereof, with tongue members. The front tongue members are provided at a 90 degree spacing from the rear tongue members. Thus, when connected, adjacent joint members 114a are rotated relative to each other by 90 degrees. Adjacent joint members 114a are connected by rotatably securing tongue members on adjacent joint members 114a using rivets 114b.

The edges of the joint members 114a are formed such that the distance between the edges of the joint members 114a is greatest at a point 90 degrees from the tongue members and is smallest at the connection between the tongue members.

Accordingly, the joint members 114a can rotate about the rivets 114b until adjacent edges contact, thus, the free-bending portion 114 can be caused to bend, as a whole, in a desired direction.

The treatment accessory 100 constructed as described above is used as described in the following.

Figure 12:
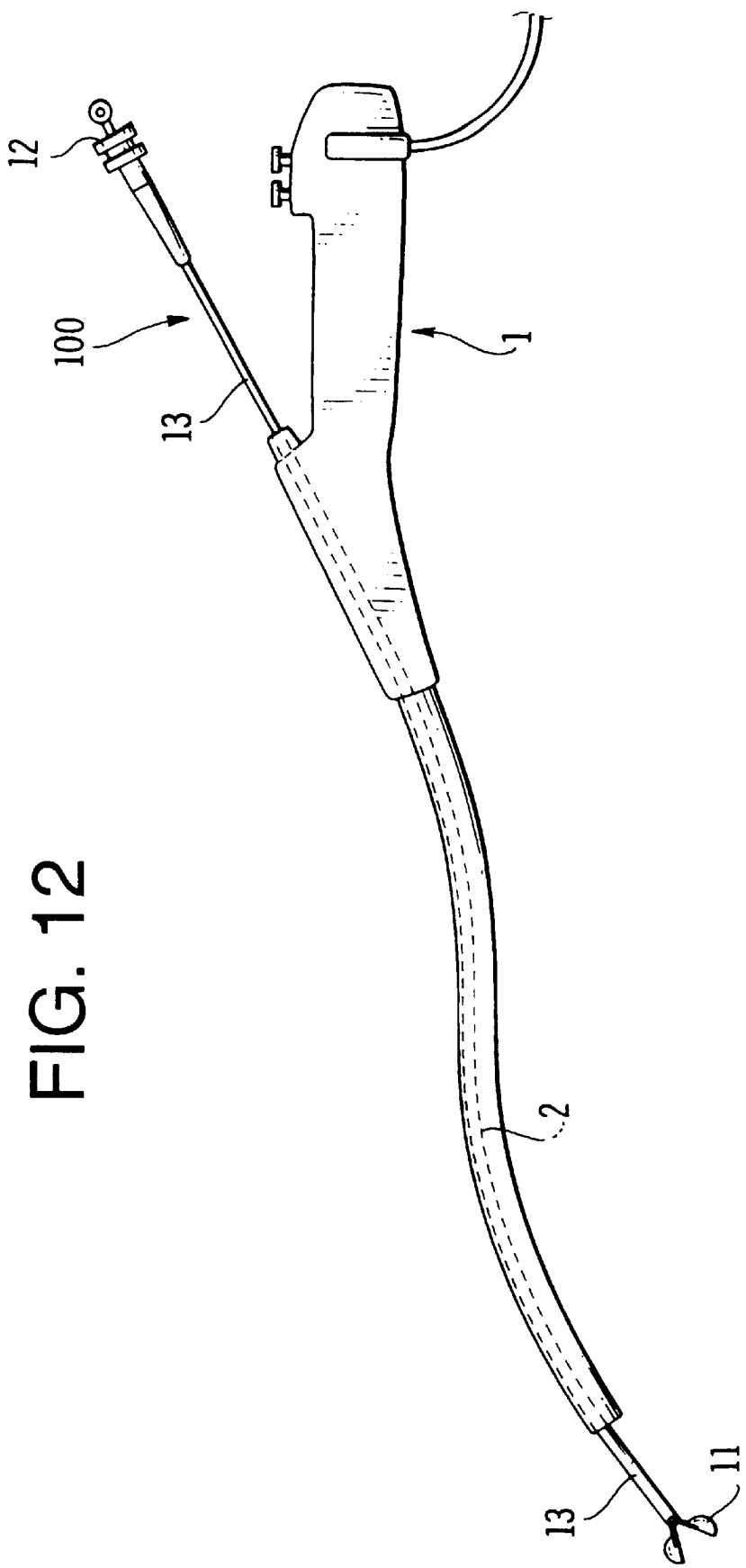
FIG. 12 is a side view of an endoscope having a forceps channel in which the treatment accessory of FIG. 11 is inserted.

As shown in FIG. 12, during use, the treatment accessory 100 is slidably inserted in the forceps channel 2 of the endoscope 1.

Figure 13:
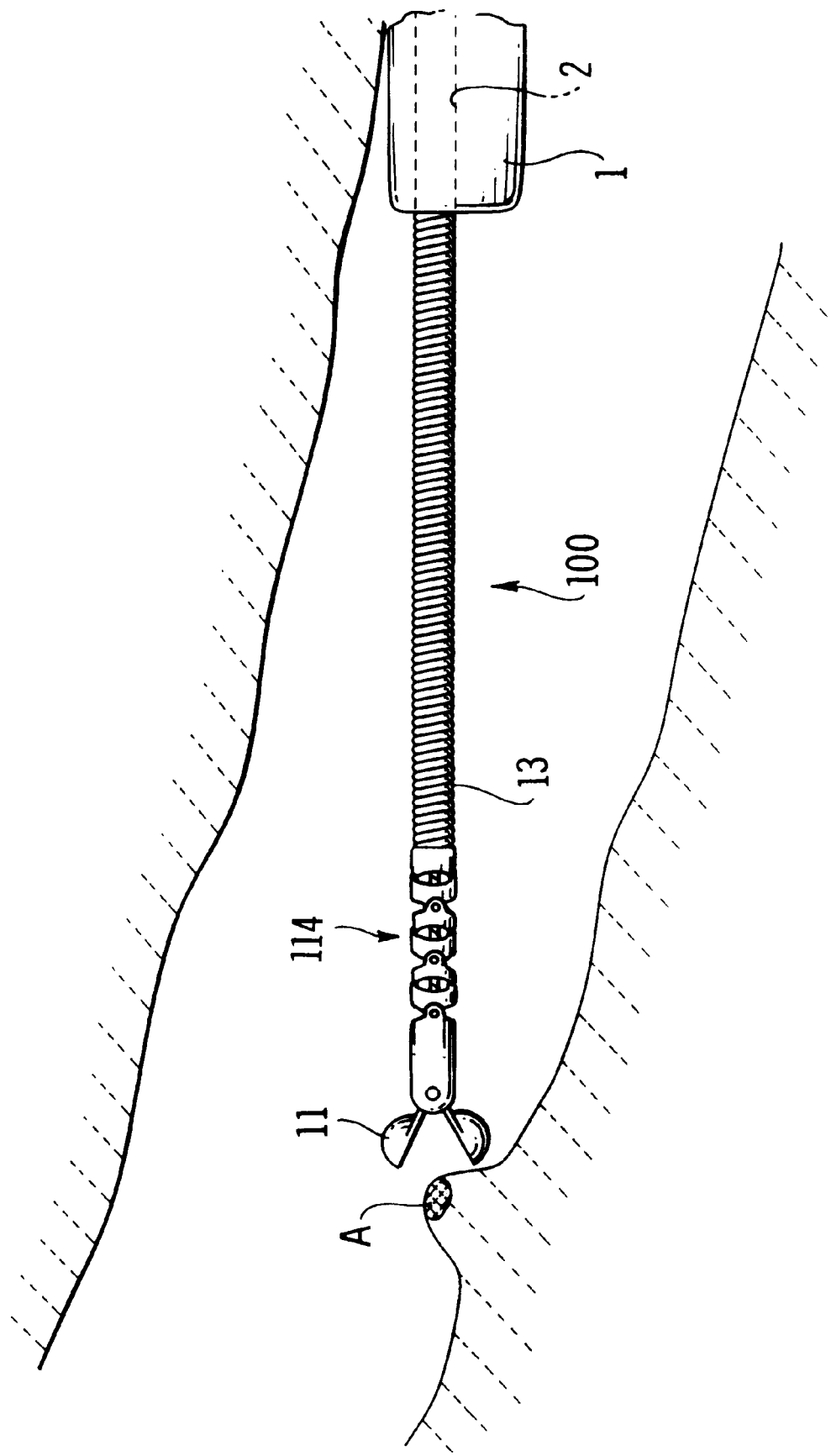
FIG. 13 is a schematic view illustrating the operation of the treatment accessory shown in FIG. 11.

As shown in FIG. 13, the distal end of the treatment accessory 100 is extended from the forceps channel 2 of the endoscope 1, and one of the forceps cups 11b is pressed against a portion of tissue near the affected part A.

Figure 14:
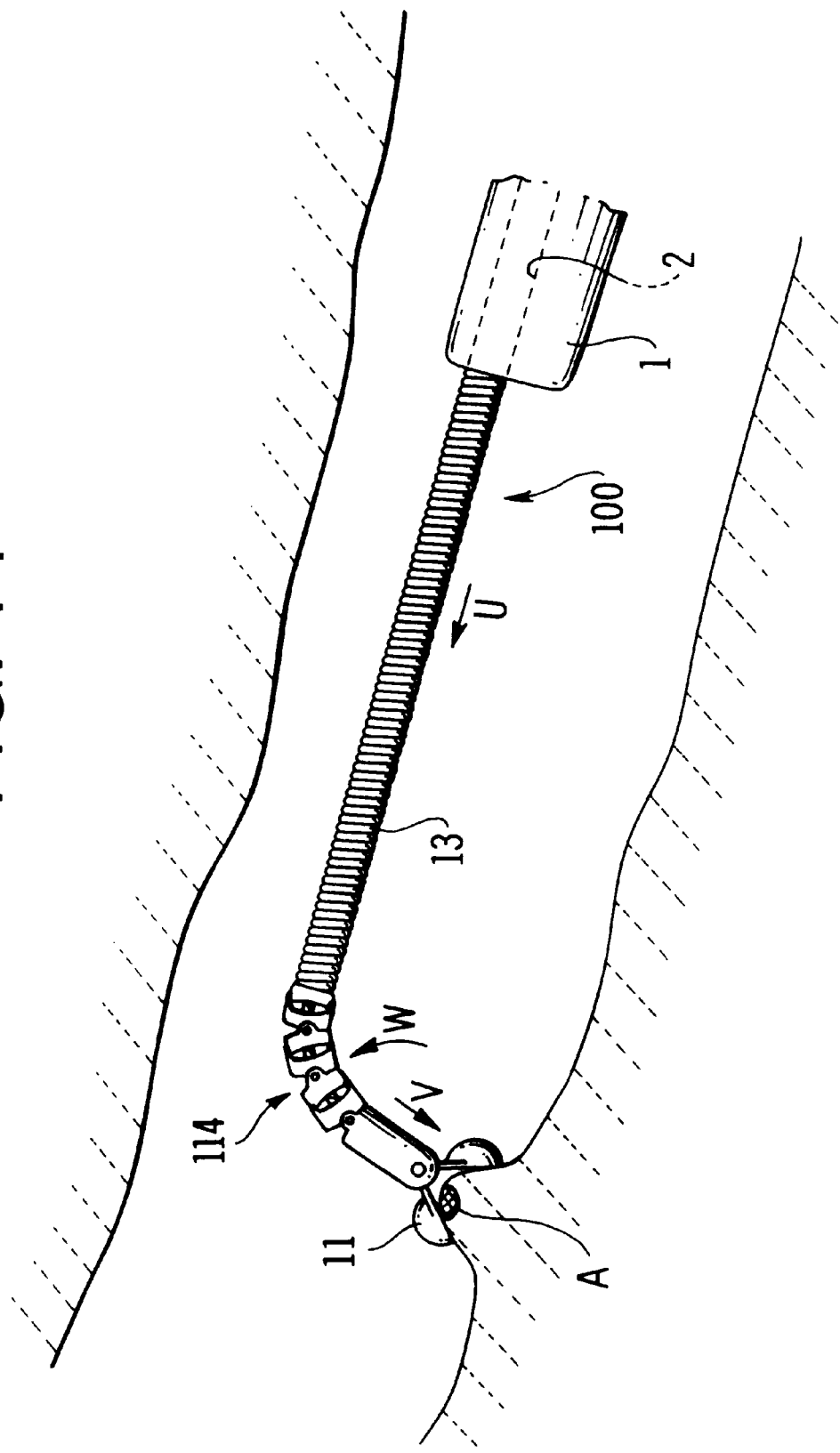
FIG. 14 is a schematic view illustrating the operation of the treatment accessory shown in FIG. 11 in a different state from that shown in FIG. 13.

Then, as shown in FIG. 14, the flexible shaft 13 is further extended from the forceps channel 2 (i.e., moved in the direction of the arrow U) causing the free-bending portion 114 to bend (arrow W), using the treating device 11, which is pressed against the affected portion A as a fulcrum. Thus, the orientation of the treating device 11 changes such that the treating device 11 directly faces the affected part A (i.e., in the direction of the arrow V).

As a result, when, as in this example, the treating device 11 is biopsy forceps, it is easier to collect biopsy tissue from a desired location. If the treating device 11 is a device other than biopsy forceps, the affected part A can be treated appropriately according to its location.

With regard to the first and second embodiments, it should be noted that, if the free-bending portion 14, 114 is designed to bend excessively, with reference to the second embodiment shown in FIG. 14, when the flexible shaft 13 is pushed in the direction of the arrow U, the free-bending portion 114 may only bend further, and not provide sufficient force to the treatment device 11 in the direction of the arrow V, i.e., the treatment device 11 may not appropriately face and be pressed against the affected part A.

As such, it has been determined that, if a bending angle exceeds 70 degrees, the force with which the treatment device 11 is pressed against the affected part A is too low and treatment of the affected part A may not be done appropriately. Therefore, it is preferable that the free-bending portion 14, 114 is formed such that the maximum bending angle is equal to or less than 70 degrees.

FIGS. 15 to 18 show examples of when the treatment accessory 10 according to the first embodiment is used. The treatment accessory 100 of the second embodiment may be used in a similar fashion.

Figure 15:
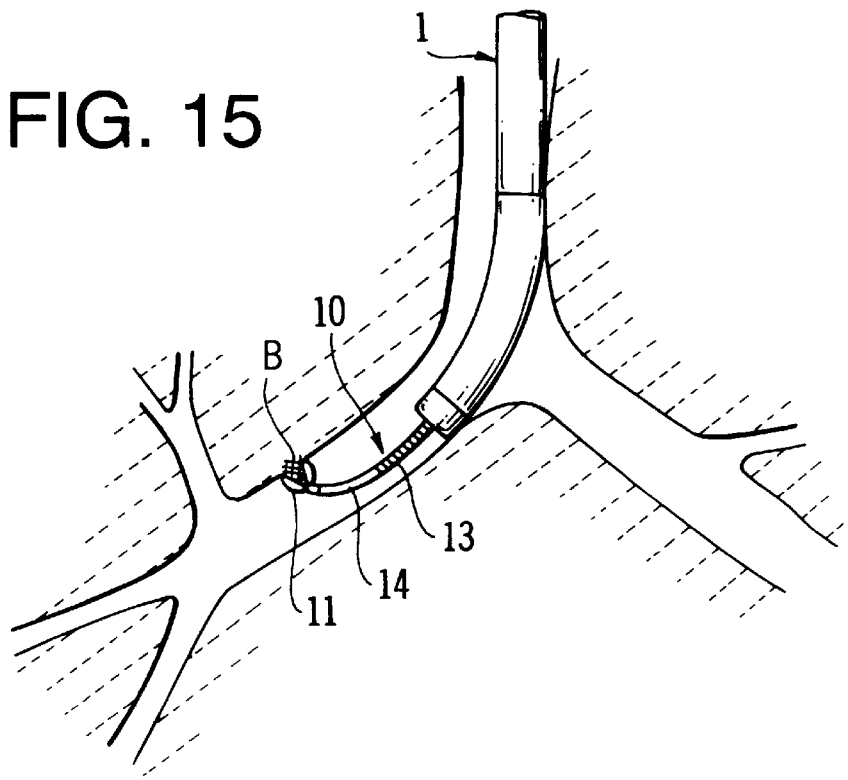
FIG. 15 is a schematic view illustrating the use of the treatment accessory shown in FIG. 1 in a bronchial tube.

FIG. 15 shows the use of the treatment accessory 10 in a bronchial tube. The treatment accessory 10 is extended from the endoscope 1 to treat an affected part B. Since the diameter of a bronchial tube is 12 to 16 mm at the largest portion, the length of the free-bending portion 14 of a treatment accessory 10 for bronchial tubes is preferably 10 mm or less.

Figure 16:
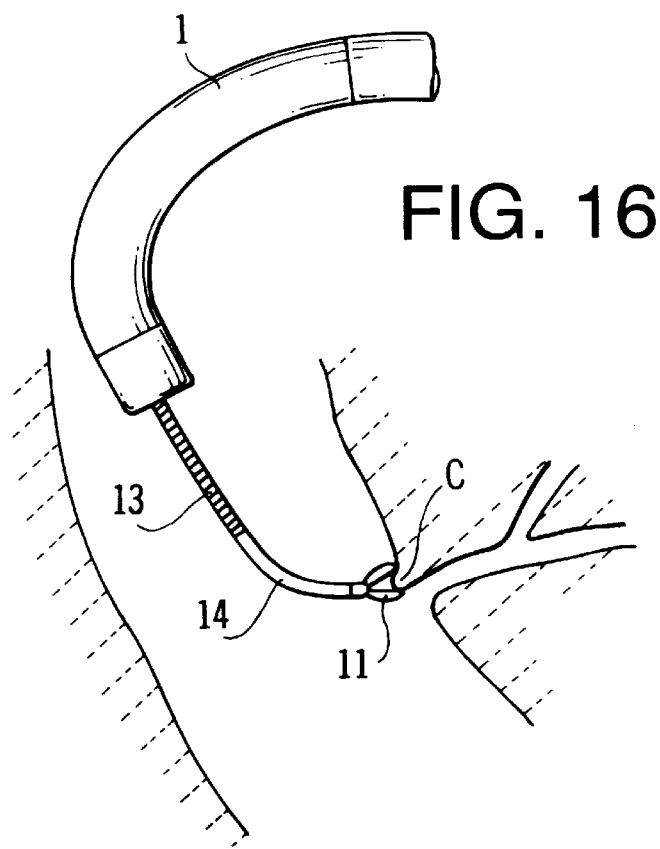
FIG. 16 is a schematic view illustrating the use of the treatment accessory shown in FIG. 1 in a duodenum.

In FIG. 16, in a duodenum, an affected part C is treated with the treatment accessory 10. Since the diameter of the duodenum is 40 to 60 mm, the length of the free-bending portion 14 of the treatment accessory 10 for the duodenum is preferably 30 mm or less.

Figure 17:
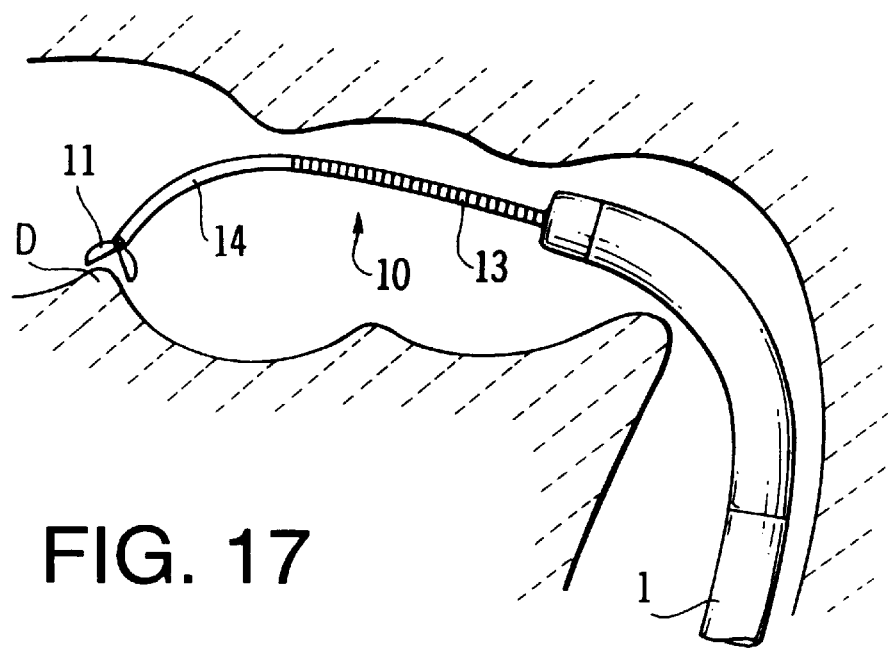
FIG. 17 is a schematic view illustrating the use of the treatment accessory shown in FIG. 1 in a colon.

In FIG. 17, in a colon, an affected part D is treated with the treatment accessory 10. Since the diameter of the colon is approximately 70 mm, the free-bending portion 14 of the treatment accessory 10 for the colon is preferably 40 mm or less.

Figure 18:
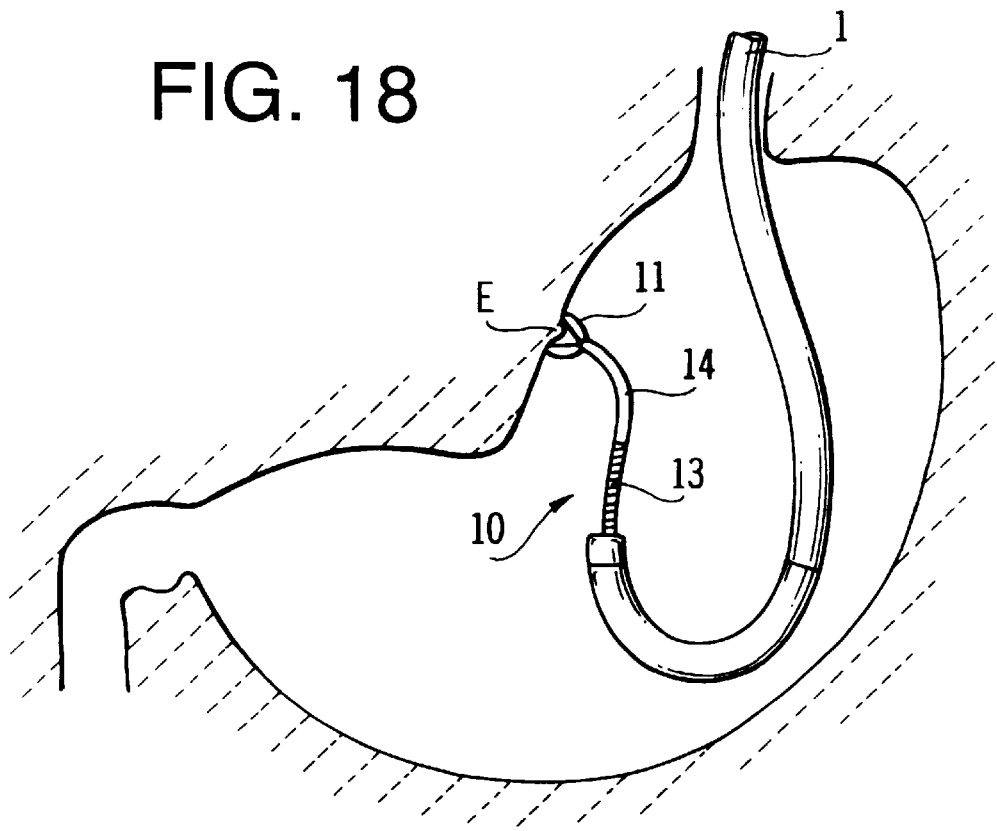
FIG. 18 is a schematic view illustrating the use of the treatment accessory shown in FIG. 1 in a stomach.

In FIG. 18, an affected part E in a stomach is treated using the treatment accessory 10. Since the capacity of the stomach is about 1.4 liters, the length of the free-bending portion 14 is preferably 50 mm or less.

Figure 19:
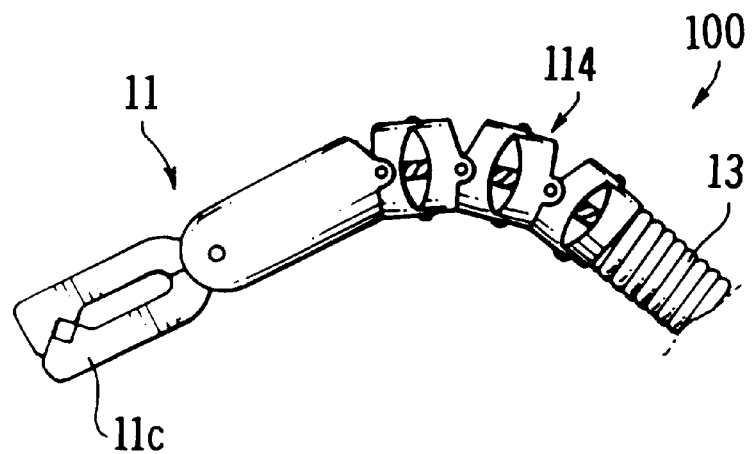
FIG. 19 is a side view of a distal end of a treatment accessory according to the second embodiment having a grasping forceps as a treating device.
Figure 20:
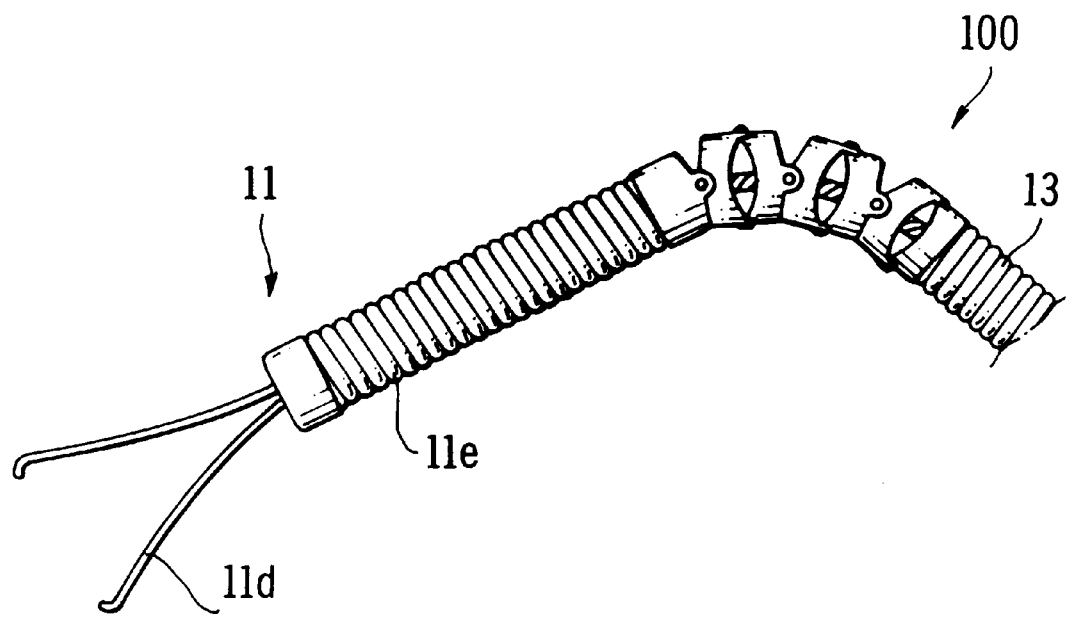
FIG. 20 is a side view of a distal end of a treatment accessory according to the second embodiment having a grasping device as a treating device.
Figure 21:
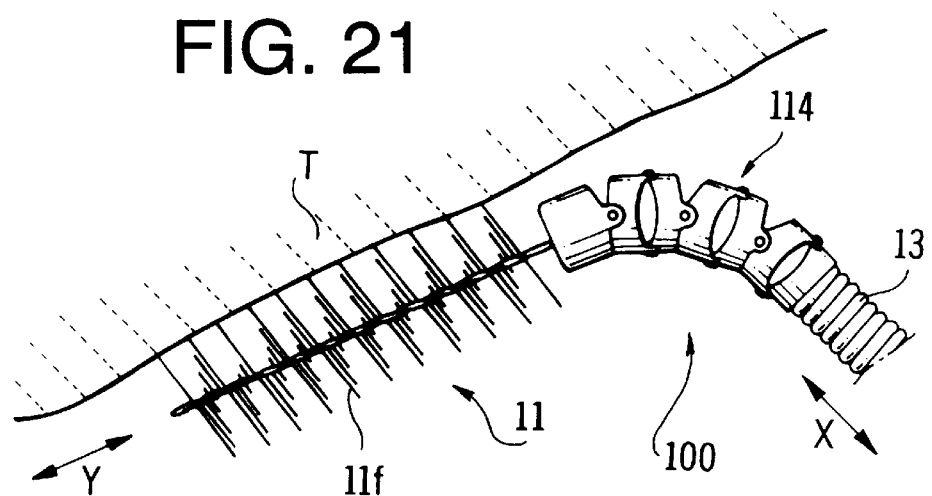
FIG. 21 is a side view of a distal end of a treatment accessory according to the second embodiment having a brush as a treating device.

Generally, the treatment accessory 10 is not used for organs larger than the stomach, thus, the length of the free-bending portion 14 is generally 50 mm or less, depending on the purpose of the treatment accessory 10, As with the treatment accessory 10 of the first embodiment, the treatment accessory 100 of the second embodiment may be provided with a variety of treating devices 11. As shown in FIG. 19, the treating device 11 may be a pair of grasping forceps 11c (alligator forceps). Alternatively, as shown in FIG. 20, the treating device 11 may also be a grasping device lid having a pair of flexible wires. Further alternatively, as shown in FIG. 21, the treating device 11 may be a brush 11f, for brushing cytology. Similar to as described above for the first embodiment, by using the free-bending portion 114, even if the flexible shaft 13 cannot be arranged parallel to a tissue surface T, the brush 11f can still be positioned such that, by moving the flexible shaft 13 in relation to the direction in which the flexible shaft extends (i.e., the direction shown by arrow X), the brush 11f moves along the tissue surface T (i.e., the direction shown by arrow Y) to scrape human tissue.

Figure 22:
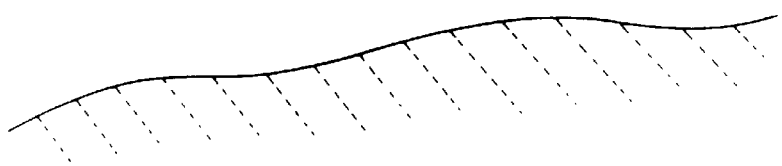
FIG. 22 is a sectional view of a distal end of a treatment accessory according to the second embodiment having an alternative structure.

The structure of the free-bending portion 114 is not limited to the structure described above. FIG. 22 shows an alternative free-bending portion 114M. In FIG. 22, the free-bending portion 114M is formed as a cylindrical elastic tube 14c, made from a flexible material such as silicon rubber or the like, having a loosely-wound metal coil 14d enclosed therein.

Figure 23:
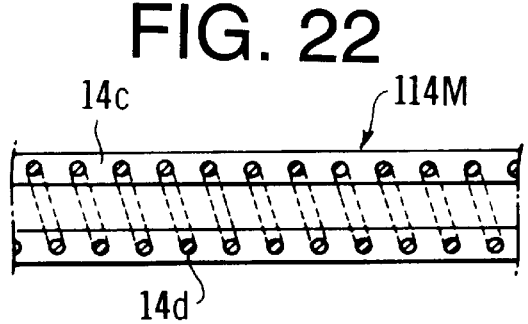
FIG. 23 is a sectional view of a distal end of a treatment accessory according to the second embodiment having another alternative structure.

FIG. 23 shows another alternative free-bending portion 114N, wherein a mesh wire tube 14e is coated with a flexible material 14f, such as silicon rubber or the like.

According to the second embodiment, since the treatment accessory 100 is provided with a flexible shaft that is provided with a free-bending portion 114, 114M, 114N at the distal end thereof, the treatment accessory 100 has a simple structure allowing the treating device 11 to be more easily positioned with respect to the affected part A. Further, since the treatment accessory 100 does not require an extra manipulation wire for controlling the curvature of the shaft, the flexible shaft 13 is flexible and small enough to be easily inserted inside the forceps channel 12. Still further, with the treatment accessory 100 of the second embodiment, the free-bending portion 114, 114M, 114N can bend in any direction allowing the treating device 11 to be more easily and accurately positioned with respect to the affected part A.

Figure 25:
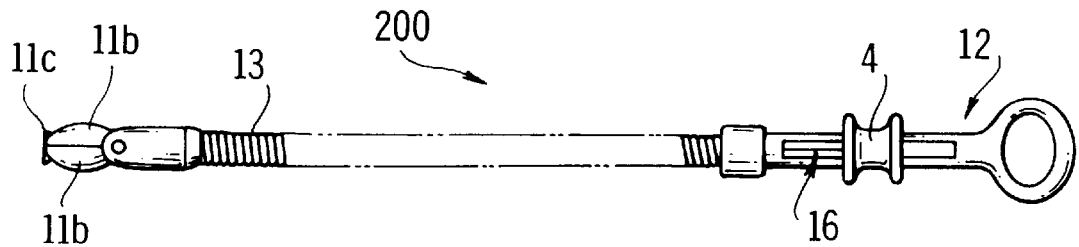
FIG. 25 is a side view of the treatment accessory according to the third embodiment.

FIG. 25 shows a treatment accessory 200 for an endoscope according to a third embodiment. Similar to the above embodiments, the treatment accessory 200 includes the flexible shaft 13 made from, for example a closely wound stainless-steel coil, the treatment device 11 provided at the distal end of the shaft 13 and the manipulation portion 12 provided at the proximal end of the shaft 13. In this embodiment, the treatment device 11 is a pair of biopsy forceps, however, other treatment devices having a similar grasping, cutting function may also be provided.

Figure 24:
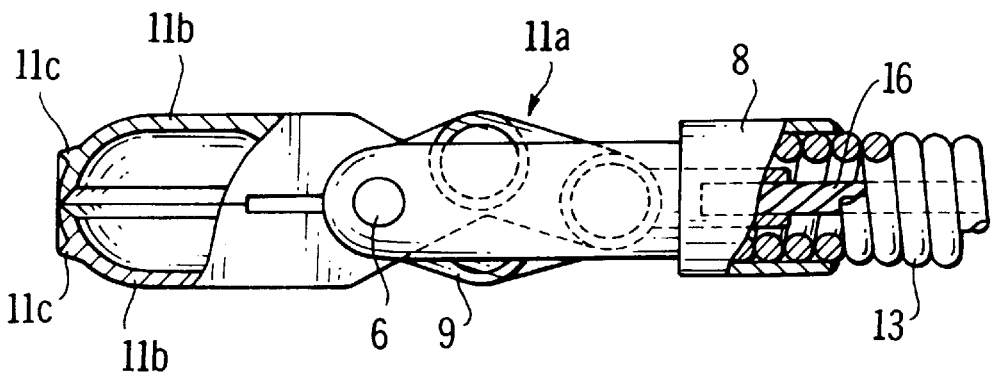
FIG. 24 is a sectional side view of a distal end of a treatment accessory according to a third embodiment of the invention.

FIG. 24 shows a detailed arrangement of the treatment device 11. The treatment device 11 includes the pair of forceps cups 11b which are rotatably mounted to a link shaft 6. The forceps cups 11b and the link shaft 6 are connected through a linking mechanism 11a with the wire 16 such that, by operating a slider 4 provided at the manipulation portion 12 of the treatment accessory 200, the wire 16 moves along a central axis of the treatment accessory 200 and accordingly opens and closes the forceps cups 11b.

The forceps cups 11b are formed, such that, when closed, the forceps cups 11b have an elliptical shape, one of the short ends of which is attached to the link shaft 6, the other of the short ends being a tip portion. The edges of the forceps cups 11b that meet when the forceps cups 11b are closed are formed as cutting blades.

The treating device 11 also includes a main body 8 that is fixedly connected at the distal end of the shaft 13. The link shaft 6 is provided at the distal end portion of the main body 8. The main body 8 is formed such that a rear portion (the right-hand side in FIG. 24) thereof is cylindrical, and a front portion (the left-hand side in FIG. 24) has parallel arms spaced to define a slit.

The forceps cups 11b are each formed to include an arm 9 which extends to the rear side (right-hand side in FIG. 24). The arms 9 form a part of the pantograph-type link mechanism 11a. Further, the distal end of the wire 16 is connected to the rear end of the link mechanism 11a. In this way, the forceps cups 11b are connected to the wire 16 by a known linking mechanism, such as the pantograph-type link mechanism 11a.

Figure 26:
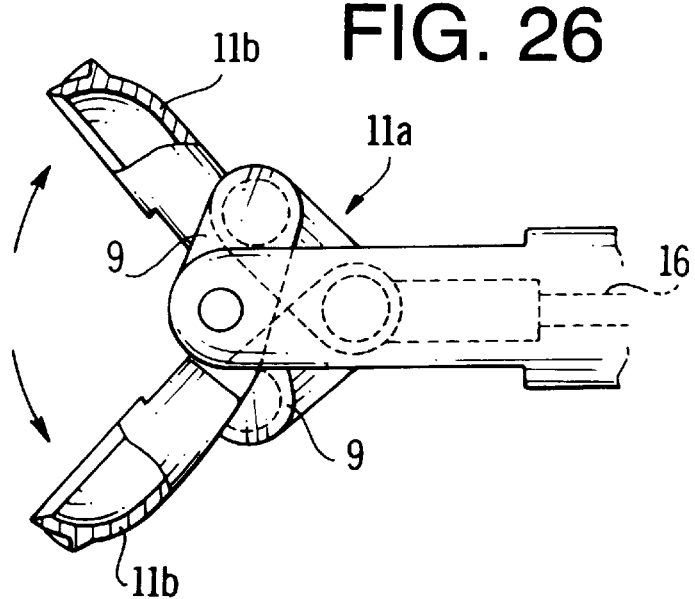
FIG. 26 is a side view of a distal end of the treatment accessory of FIG. 24 when a treating device is opened.

Accordingly, when the slide 4 is operated so that the wire 16 is pushed out of the flexible shaft 13, the link mechanism 11a operates to open the forceps cups 11b as shown in FIG. 26. Conversely, when the wire 16 is pulled, the forceps cups 11b are drawn closed as shown in FIG. 24. If tissue or the like is located at the forceps cups 11b during closing, the tissue is cut by the blades on the forceps cups 11b and collected inside the forceps cups 11b.

Figure 27:
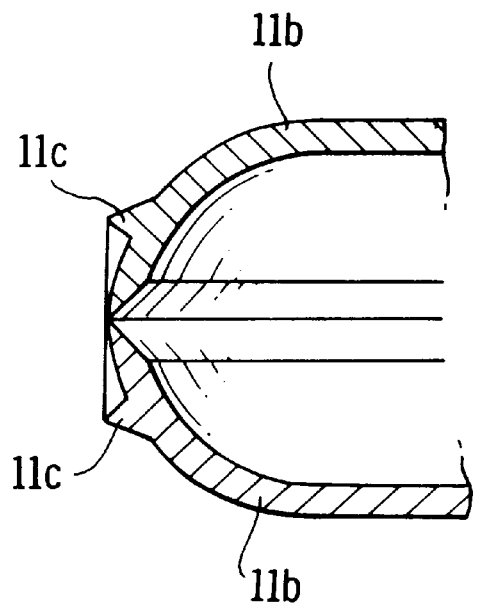
FIG. 27 is a sectional side view of forceps cups of the treatment accessory of FIG. 24.
Figure 28:
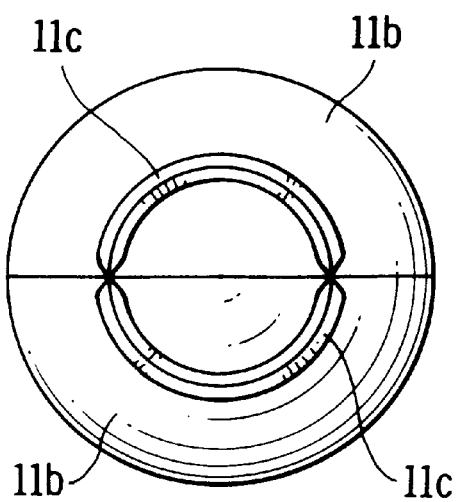
FIG. 28 is a front view of the forceps cups of FIG. 27.

As shown in FIGS. 27 and 28, a projected portion 11c is formed near the tip of each of the forceps cups 11b. The projected portion 11c is directed to a front side (left-hand side in FIG. 27). Further, as shown in FIG. 28, when the forceps cups 11b are closed, the projected portions 11c form a ring shape having a diameter that is approximately half of the maximum diameter of the forceps cups 11b when viewed from the front, as in FIG. 28. The tips of the projected portions 11c and the tips of the forceps cups 11b are substantially in the same plane. In other words, the tips of the projected portions 11c do not protrude beyond the tip of the forceps cups 11b.

Figure 29:
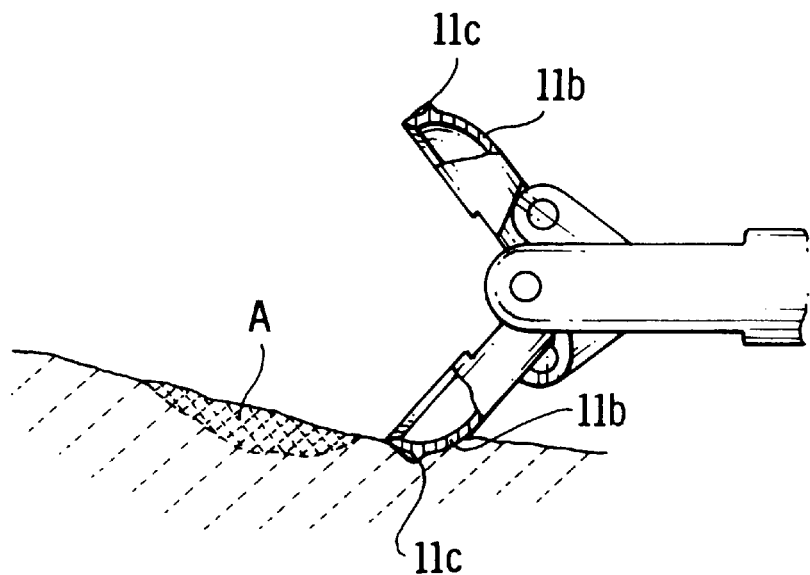
FIG. 29 is a schematic view illustrating the operation of the treatment accessory shown in FIG. 24 when preparing to collect tissue.
Figure 30:
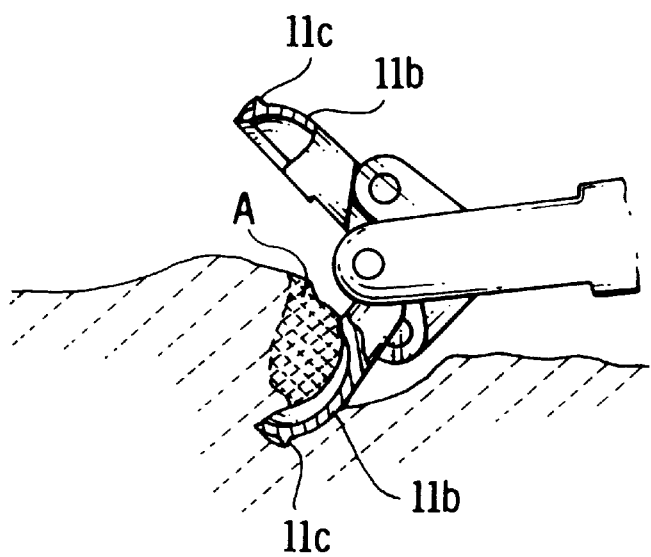
FIG. 30 is a schematic view illustrating the operation of the treatment accessory shown in FIG. 24 while collecting tissue.
Figure 31:
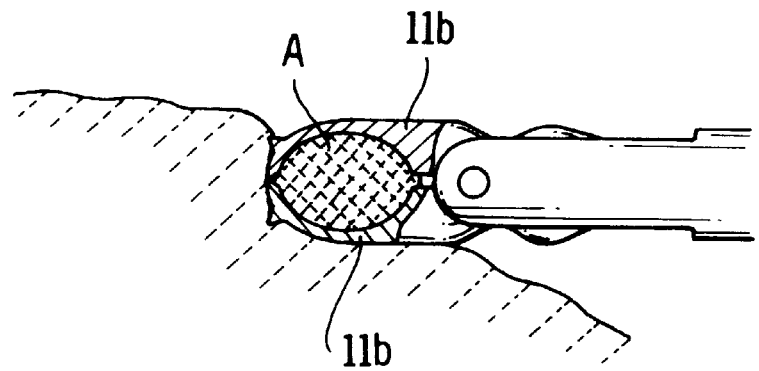
FIG. 31 is a schematic view illustrating the operation of the treatment accessory shown in FIG. 24 after collecting tissue.

FIGS. 29 through 31 show the collection of tissue or the like using the treatment accessory 200.

When an affected part A is identified, the distal end of the treatment accessory 200 is projected from the forceps channel 2 of the endoscope 1 and the forceps cups 11b are opened.

In this case, since the forceps cups 11b are directed to the affected part A from an oblique angle, first, the projected portion 11c of one of the forceps cups 11b is pushed slightly into the tissue near the affected area A as shown in FIG. 29. At this stage, since the tip of the projected portion 11c does not protrude beyond the tip of the forceps cups 11b, the tip of the forceps cups 11b is brought into contact with the tissue (see FIG. 29).

Then, the treatment accessory 200 is pushed towards the affected part A while simultaneously closing the forceps cups 11b. As shown in FIGS. 30 and 31, the tissue at the affected part A is pushed completely into the forceps cups 11b and the forceps cups 11b close around the affected part A, cutting the affected part A away inside the forceps cups 11b.

Figure 32A:
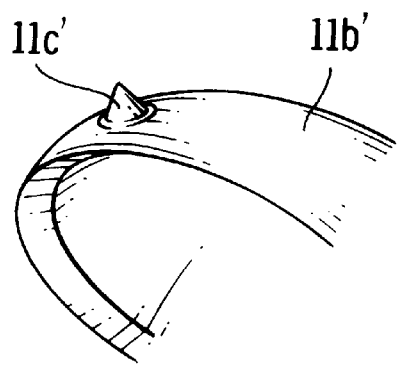
FIGS. 32A, 32B, 32C show alternative arrangements of the treatment accessory according to the third embodiment.

FIG. 32A shows an alternative forceps cup 11b' having a projected portion 11c'. In this alternative, instead of a continuous half-ring-shaped projected portion 11c as described above, at least one cone-shaped pointing portion 11c' is formed to serve a similar function.

Figure 32B:
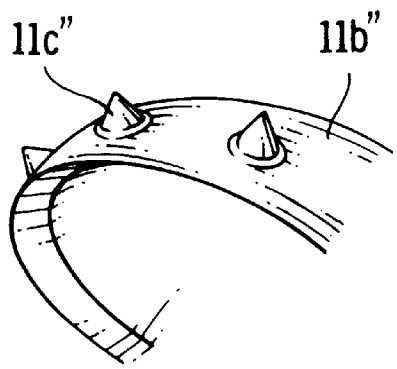

FIG. 32B shows another alternative forceps cup 11b" having projected portions 11c'. In this alternative, instead of a single projected portion 11c' as described above, a plurality of cone-shaped pointing portions 11c" are formed to serve a similar function.

Figure 32C:
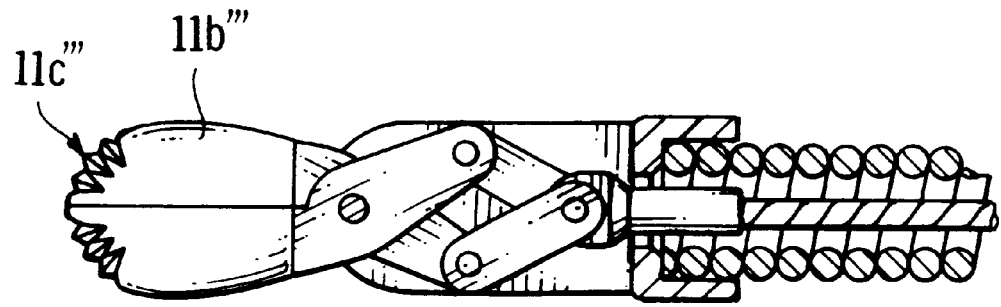

FIG. 32C shows further alternative forceps cup 11b'" having a plurality of grooves such that the forceps cup 11b'" is formed to be a corrugated surface 11c'". In this alternative, instead of a single porjected portoin 11c' or a plurality of projected portions 11c", a plurality of grooves are formed such that the surface of the forceps cup is provided with a plurality of projected parts and grooves, i.e., the suface is formed to have the corrugated surface 11c'". Such a surface also serves a similar fuction.

In the present embodiment, the treating device 11 is described as including forceps cups 11b, however, other types of treating devices can also be formed to include a projected portion 11c (or alternatives) such as described above. For example, as shown in FIG. 32C, the treating device 11 may be grasping forceps.

Figure 33:
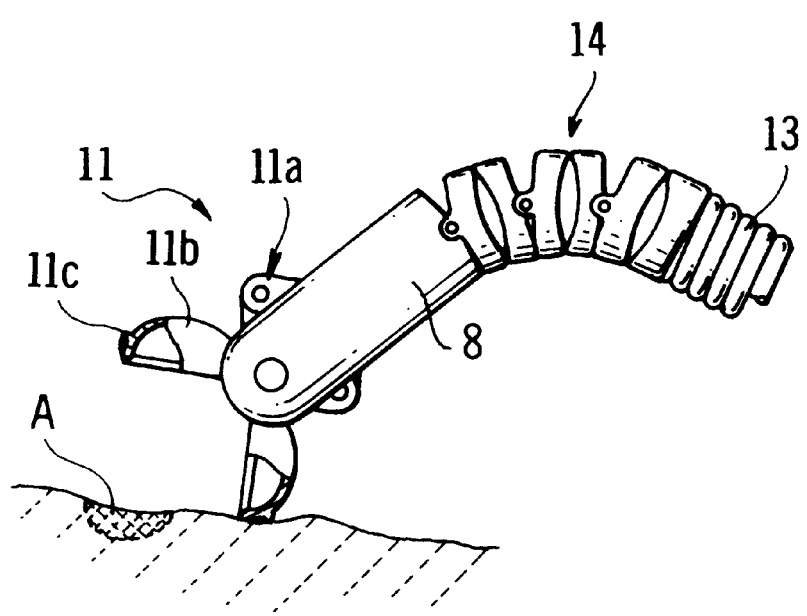
FIG. 33 is a schematic view of the treatment accessory according to the third embodiment provided with a free-bending portion described in relation to the first embodiment.
Figure 34:
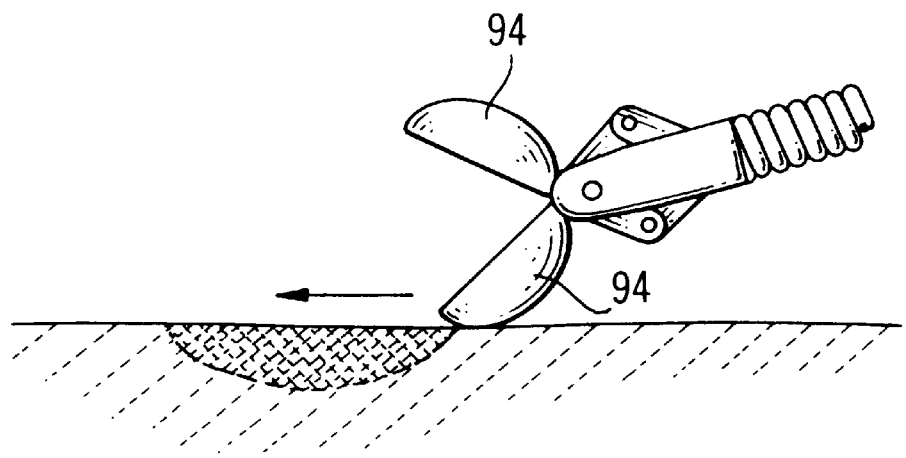
FIG. 34 is a schematic view of a distal end of a conventional treatment instrument.
Figure 35:
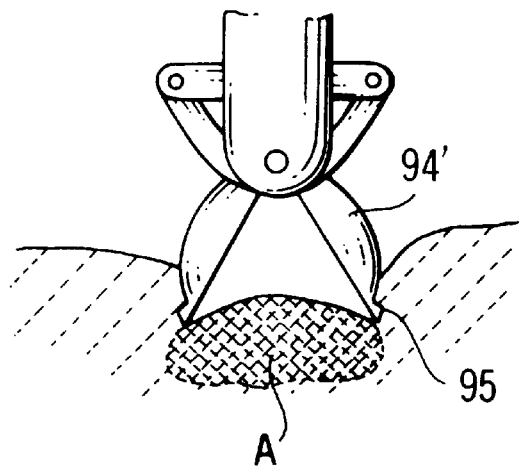
FIG. 35 is a schematic view of a distal end of a modified conventional treatment instrument.

FIG. 33 shows an arrangement of the treatment accessory 200 further provided with a free-bending portion 14 as described with respect to the first embodiment. As described above, in this case, since the treating device 11 is hooked as the projected portion 11c engages with the tissue surface, the orientation of the treating device 11 can be adjusted by bending the free-bending portion 14 until the orientation is appropriate for treating the affected portion A.

The provision of the projected portion 11c, 11c', 11c" as described above allows a treating device 11 that is obliquely directed at an affected part A to be appropriately positioned with respect to the affected part A. Further, since the projected portions 11c, 11c', 11c" are formed to not exceed the frontmost end of the treating device 11, the tissue surface is not pushed away by the projected portions 11c, 11c', 11c", and the affected part A can be cut away and collected accurately. Further, since the projected portions 11c, 11c', 11c" are arranged inside the outermost surface of the treatment device 11 as viewed from the front, the projected portions 11c, 11c', 11c" do not prevent the treatment accessory 200 from being inserted in the forceps channel 2.

Figure 37:
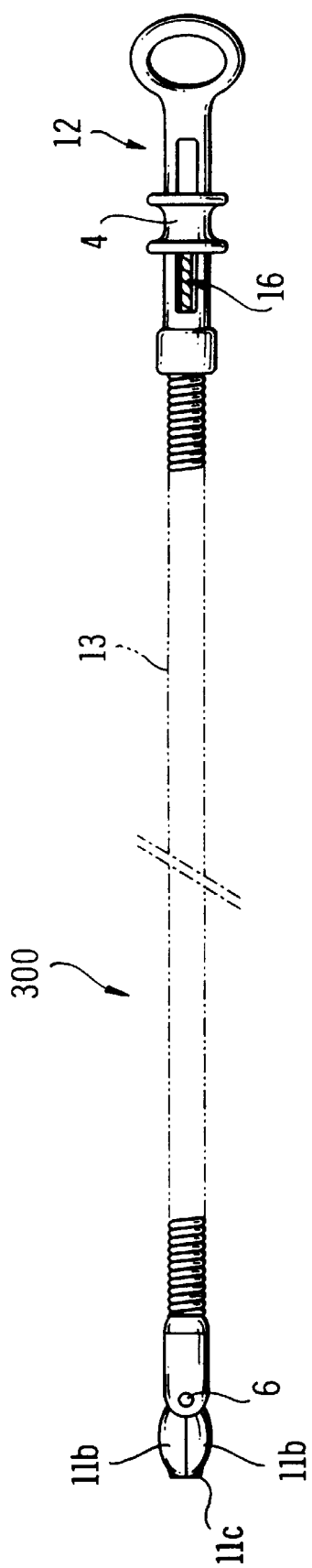
FIG. 37 is a side view of the treatment accessory according to the fourth embodiment.

FIG. 37 shows a treatment accessory 300 for an endoscope according to a fourth embodiment of the invention. The treatment accessory 300 is similar to the treatment accessory 200 of the third embodiment and identical elements are not described in detail. The treatment accessory 300 includes the flexible shaft 13, the manipulation portion 12, and the treating device 11. In this embodiment, the treating device 11 is described as a pair of biopsy forceps, however, other treatment devices having a similar grasping or cutting function may also be substituted.

Figure 36:
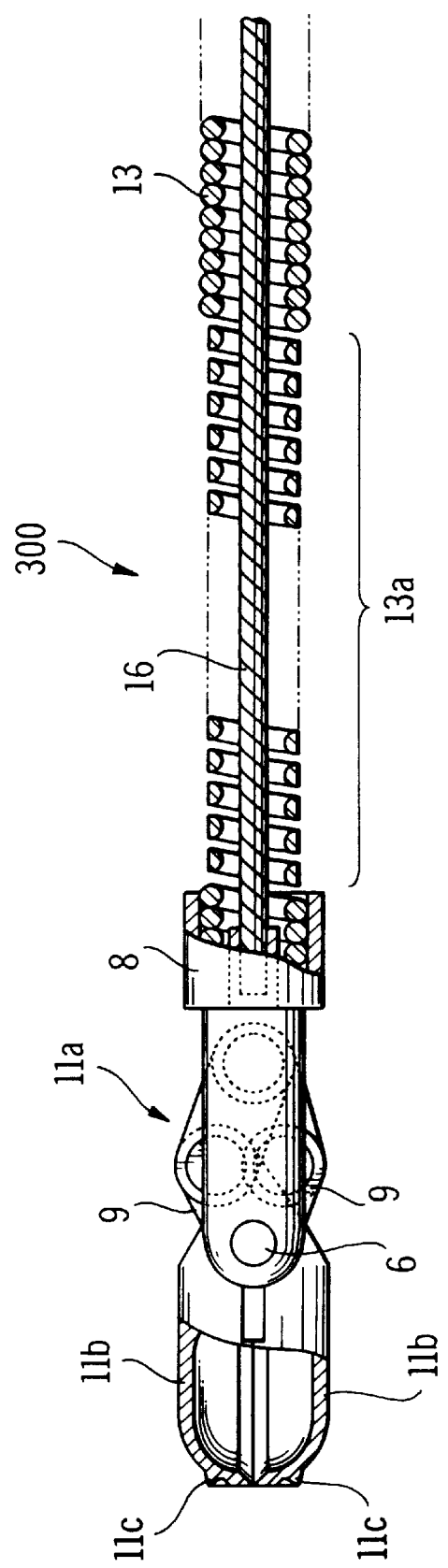
FIG. 36 is a sectional side view of a distal end of a treatment accessory according to a fourth embodiment of the invention.

FIG. 36 shows a detailed arrangement of the treating device 11. As in the third embodiment, the treating device 11 includes the pair of forceps cups 11b which are rotatably mounted to the link shaft 6. The forceps cups 11b and the link shaft 6 are connected through the linking mechanism 11a with the wire 16 such that, by operating the slider 4 provided at the manipulation portion 12, the wire 16 moves along a central axis of the treatment accessory 300 and accordingly opens and closes the forceps cups 11b. The forceps cups 11b are provided with the projection portions 11c described above.

Further, as shown in FIG. 36, the treatment accessory 300 is further provided with an easy-to-bend (ETB) portion 13a that is formed at the distal end of the shaft 13. As a specific example, the outer surface of the coil that forms the shaft 13 may be ground at the easy-to-bend portion 13a such that the coil has less sectional surface area than the other portions of the coil.

Further, the shaft 13, except for the easy-to-bend portion 13a, is preloaded such that adjacent windings in the coil contact with each other in order to increase the stiffness thereof. As a result, the shaft 13 is relatively stiff and straight while the easy-to-bend portion 1a is more flexible and can be bent relatively easily in any direction. Note that there is no operation wire provided for controlling the bending of the ETB portion 13a. In this embodiment, the flexibility of the ETB portion 13a is more than twice that of the main portion of the shaft 13. That is, when applying a force perpendicular to the axis of the shaft 13, less than half the force necessary to bend the main portion of the shaft 13 is required to bend the ETB portion 13a. Of course, if this property of flexibility can be achieved using a preloaded ETB portion 13a, such an alternative structure is also acceptable.

As an example, the length of the shaft 13 may be 1–2 meters, and the length of the ETB portion 13a may be 5–30 mm. Further, the preloading described above may be in the range of 100–150 grams.

Figure 38:
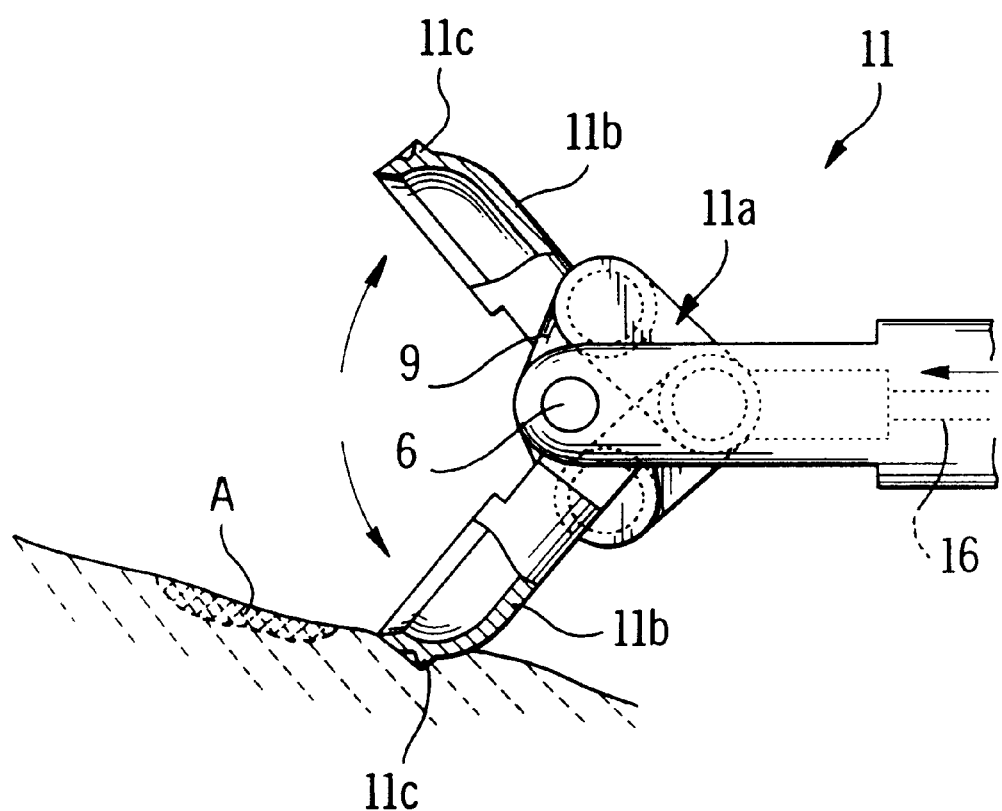
FIG. 38 is a schematic view illustrating the operation of the treatment accessory shown in FIG. 36 when preparing to collect tissue.
Figure 39:
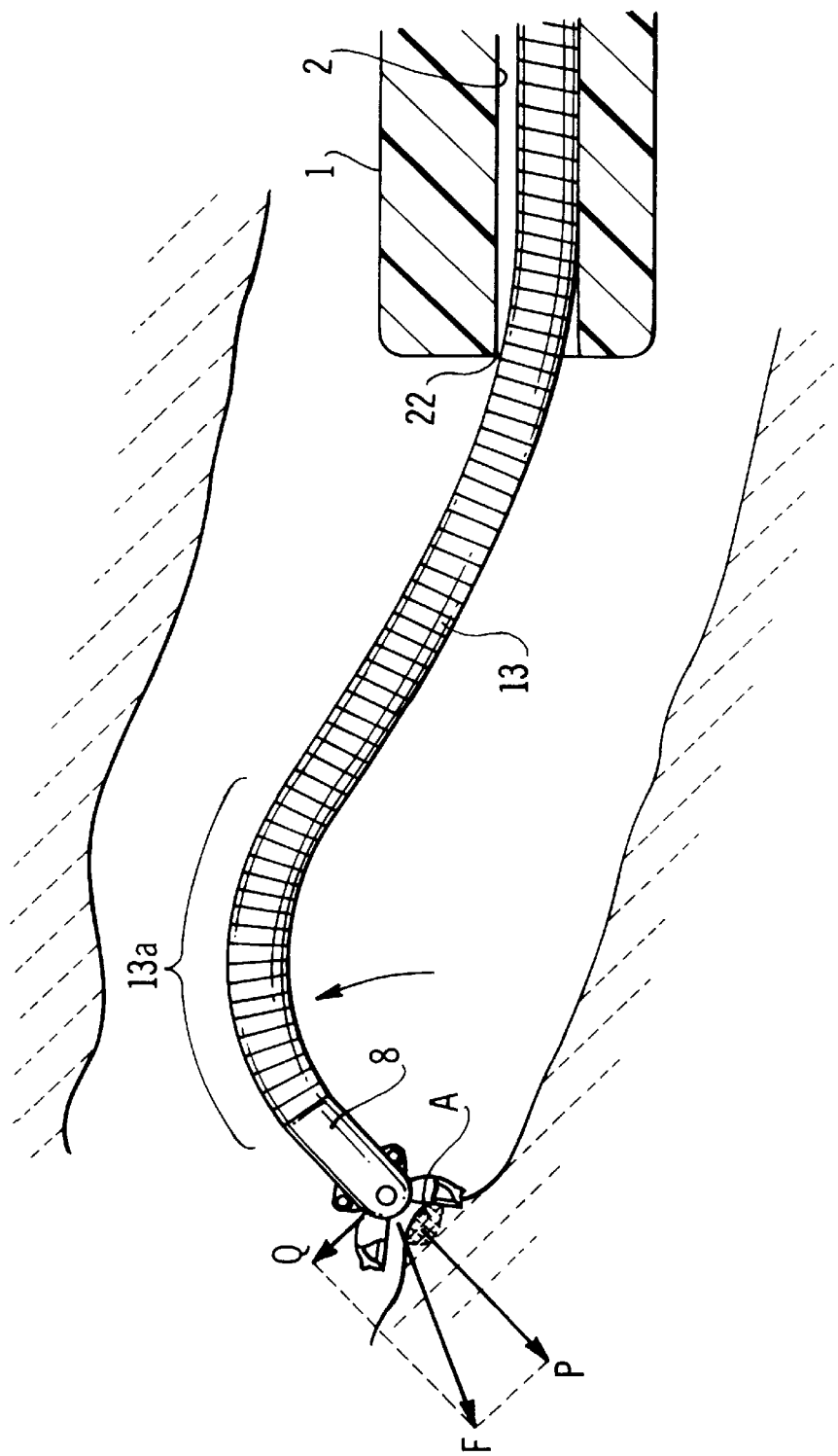
FIG. 39 is a schematic view illustrating the operation of the treatment accessory shown in FIG. 36 while collecting tissue.

FIGS. 38 and 39 show the collection of tissue using the treatment accessory 300.

When an affected part A is identified, the distal end of the treatment accessory 300 is projected from the forceps channel 2 of the endoscope 1 and the forceps cups 11b are opened.

In this case, since the forceps cups 11b are directed to the affected part A from an oblique angle, first, the projected portion 11c of one of the forceps cups 11b is pushed slightly into the tissue near the affected area A as shown in FIG. 38. At this stage, since the tip of the projected portion 11c does not protrude beyond the tip of the forceps cups 11b, the tip of the forceps cups 11b is brought into contact with the tissue.

By further pressing the shaft 13 through the forceps channel 2, the ETB portion 13a bends smoothly to form a curve smoothly connecting the outlet 22 of the forceps channel 2 to the main body 8 of the forceps cups 11b while, at the same time, the attitude of the treating device 11 is changed to approach the affected part A from above (as shown in FIG. 39). When the endoscope 1 and treatment accessory 300 are positioned as shown in FIG. 39, a force P is applied by the forceps cups 11b to the affected part A in the direction of the axis of the main body 8 and a force Q, directed perpendicular to the force P, is exerted by the ETB portion 13a due to a restoring force causing the ETB portion 13a and the shaft 13 to straighten. Thus, a resultant force F is applied to the affected part A as shown in FIG. 39.

Therefore, the forceps cups 11b are strongly pressed against the affected part A. Accordingly, in this case, in which the treatment device is the biopsy forceps, the tissue at the affected part A can be collected. Further, if another type of treatment device, other than the biopsy forceps, is used, the affected part A can be treated appropriately and accurately.

As another particular example, the length of the ETB portion 13a for an alimentary canal is preferably 30 mm or less. Note that, if the length of the ETB portion 13a is too long, the ETB portion 13a may not bend appropriately and further, in order to obtain an effect as described above, the length should be at least 5 mm.

Figure 40:
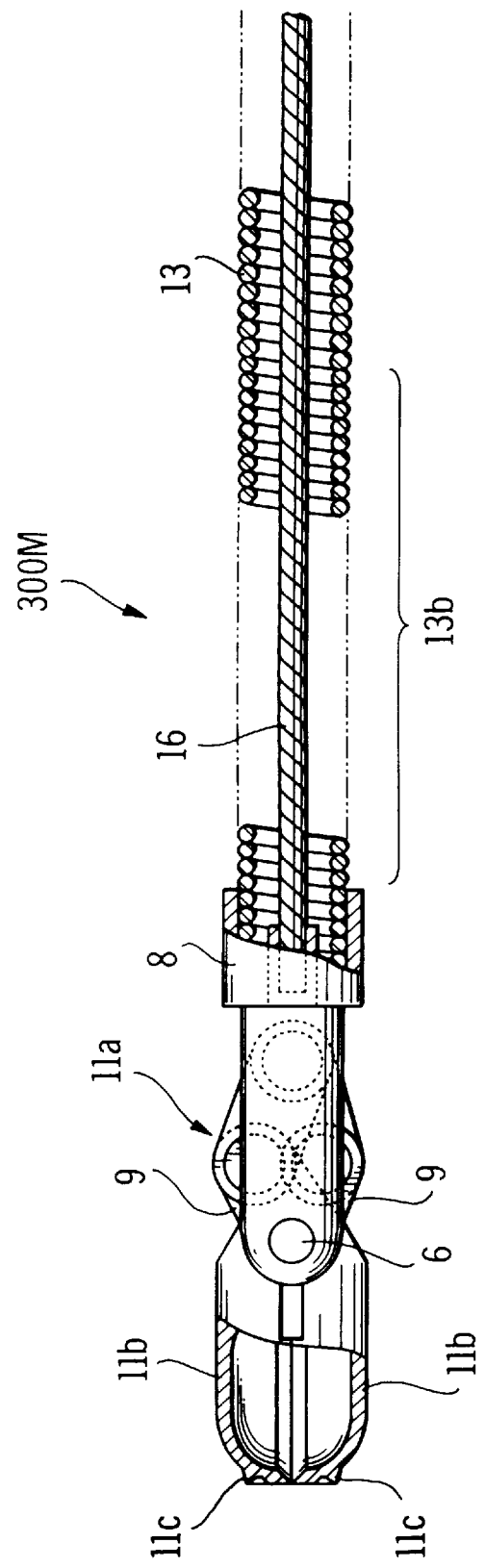
FIG. 40 is a sectional view of a distal end of a treatment accessory according to the fourth embodiment having an alternative structure.
Figure 41:
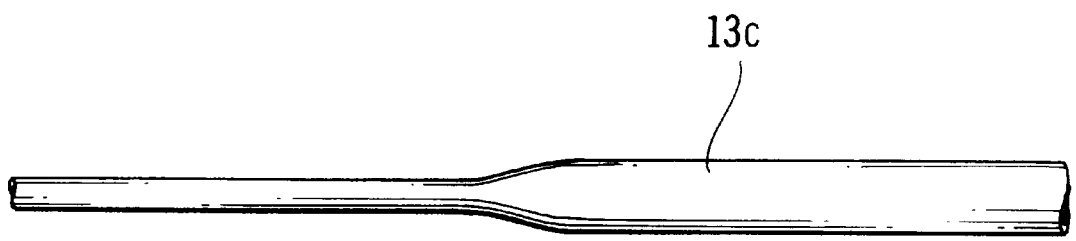
FIG. 41 is a side view of a wire used to form a shaft of the treatment accessory of FIG. 40.

FIG. 40 shows an alternative treatment accessory 300M wherein an ETB portion 13b is formed using a coil that has a smaller diameter than the diameter of the main portion of the shaft 13. This can be achieved by using a wire 13c, as shown in FIG. 41, which has a diameter that changes at a predetermined point.

As above, preferably, there should be no preloading at the ETB portion 13b. However, if the flexibility of the ETB portion 13b will be more than twice that of the main portion of the shaft 13 even after preloading, preloading at the ETB portion 13b can be performed.

In this alternative, the ETB portion 13b is described as a closely wound portion, however, it is also possible to form the ETB portion 13b as a less dense portion where the adjacent windings have spaces therebetween.

As with the previous embodiment, the projected portion 11c is not limited to the examples described, and, for example, may be modified as described above or according to the nature of the affected part A. For example, if the affected part includes relatively hard material such as a tumor or the like, or if the affected part is located at a slippery area (e.g., mucous covered surface), the projected portion 11c may be modified accordingly in order to firmly fix the position of the treatment device 11 with respect to the affected part.

In this embodiment, since the shaft 13 includes the ETB portion 13a, even if the treatment device 11 approaches the affected part A from an oblique angle, by pressing the shaft 13 further out of the forceps channel 2, the attitude of the treatment device 11, e.g., the forceps cups 11b, can be adjusted to be appropriately positioned with respect to the affected part A.

Further, since no extra wire is required for control of the ETB portion 13a, the treatment accessory 300 is thin and can be inserted in the forceps channel 2 easily.

Figure 42:
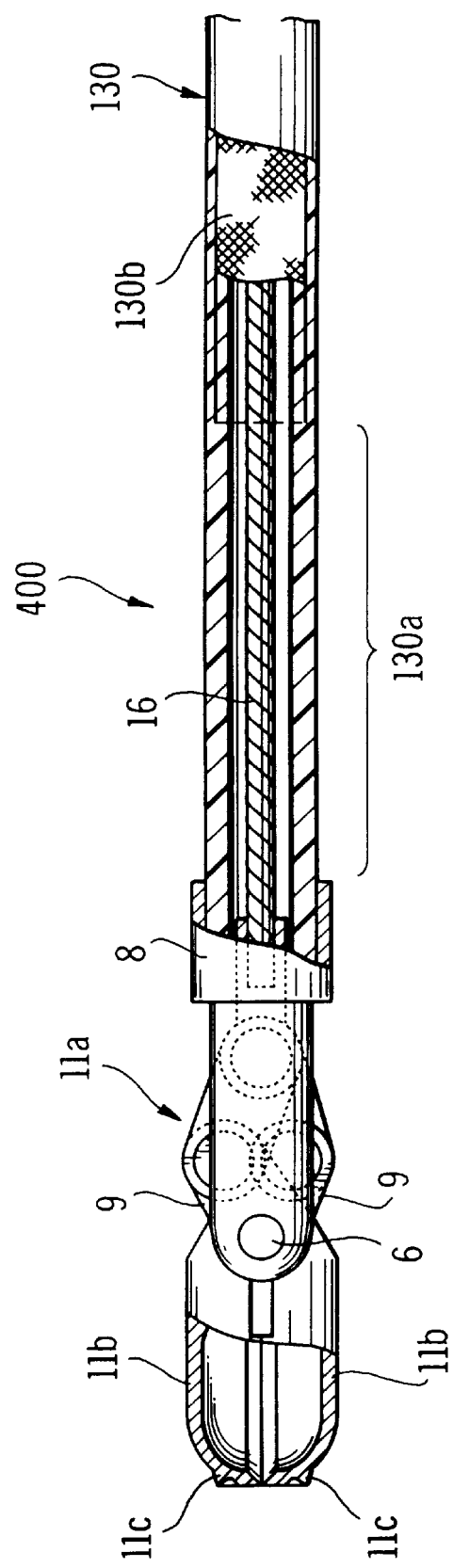
FIG. 42 is a sectional side view of a distal end of a treatment accessory according to a fifth embodiment of the invention.

FIG. 42 shows a treatment accessory 400 according to a fifth embodiment. The treatment accessory 400 is similar to the treatment accessory 300 of the fourth embodiment except that the treatment accessory 400 includes a flexible shaft 130 which is a tube made from a Teflon resin such as PTFE, a FEP-fluorocarbon resin, such as PFA; a polyethylene resin such as HDPE; or another synthetic resin, such as nylon. Other elements, including the treating device 11, are the same as the fourth embodiment.

The shaft 130 is provided with a mesh tube 130b made of mesh metal or meshed stiff plastic wires in order to increase the stiffness of a main portion of the shaft 130. An easy-to-bend (ETB) portion 130a is provided at the distal end of the shaft 130 that does not include the mesh tube 130b. As a particular example, the length of the shaft 130 is 1–2 m, and the length of the ETB portion 130a is 5–30 mm.

Similar to the fourth embodiment, the shaft 130 is designed such that the flexibility of the ETB portion 130a is twice that of the main portion of the shaft 130. The operation of the treatment accessory 400 is also similar to that of the treatment accessory 300 of the previous embodiment.

Figure 43:
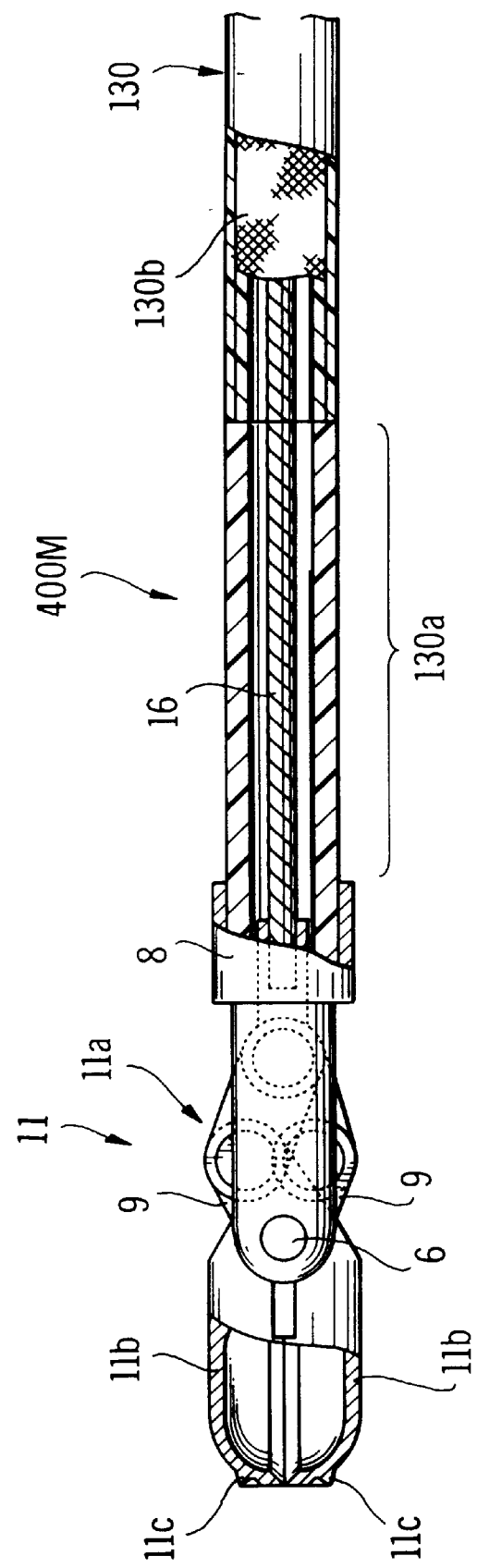
FIG. 43 is a sectional view of a distal end of a treatment accessory according to the fifth embodiment having an alternative structure.

FIG. 43 shows an alternative arrangement in which the ETB portion 130a is formed separately from the shaft 130 and the ETB portion 130a and the shaft 13 are then connected by, for example, fusing resin together to obtain a sufficient bonding strength and endurance, or alternatively, using a metal pipe (not shown) or the like, such that the ends of the shaft 13 and the ETB portion 130c are adhered on the outer surface or inner surface of the metal pipe.

Figure 44:
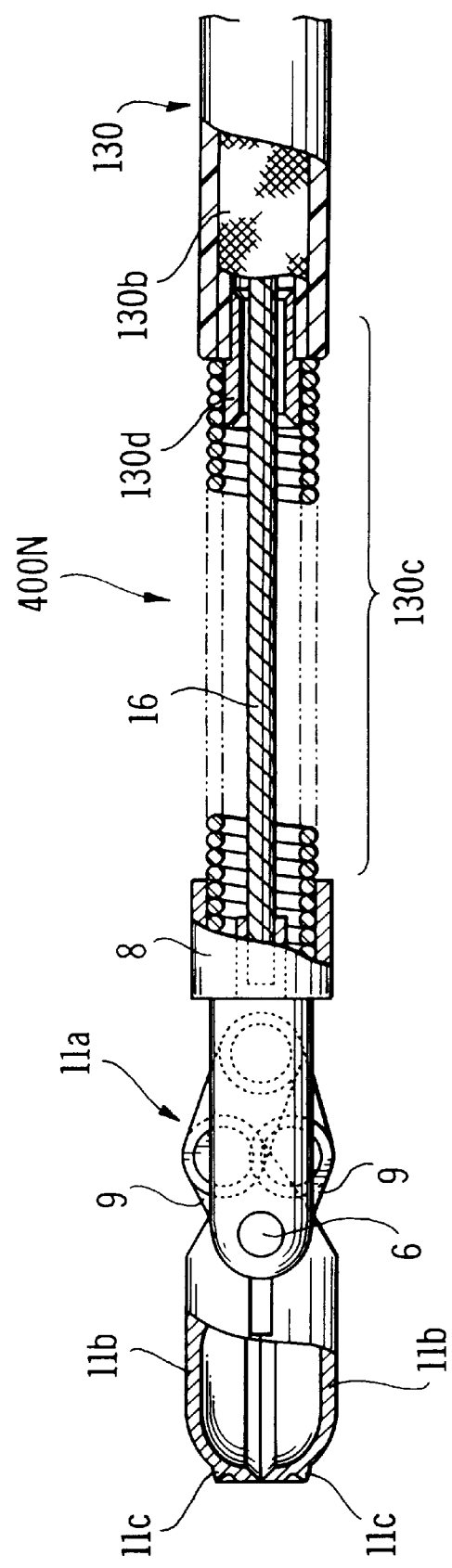
FIG. 44 is a sectional view of a distal end of a treatment accessory according to the fifth embodiment having another alternative structure.

FIG. 44 shows another alternative arrangement in which the shaft 130 is made of the synthetic resin and an ETB portion 130c is made of a coiled-wire pipe. As above, the ETB portion 130c uses coiled-wire pipe that is designed to have a relatively small diameter and flexibility that is twice that of the shaft 130. In this arrangement, the shaft 130 and the ETB portion 130c are connected using, for example, a metal pipe 130d provided inside both the shaft 130 and the ETB portion 130c.

Figure 45:
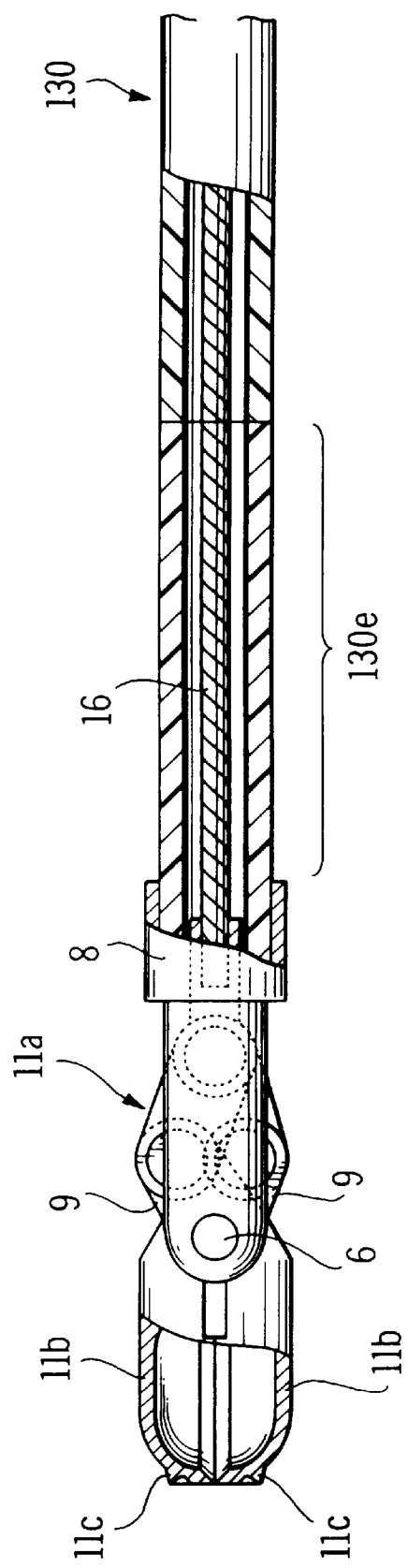
FIG. 45 is a sectional view of a distal end of a treatment accessory according to the fifth embodiment having yet another alternative structure.

FIG. 45 shows yet another alternative arrangement in which the shaft 130 and the ETB portion 130e are formed separately of synthetic resins in order to have different flexibility values. As long as the flexibility condition described above, i.e., that the ETB portion 130e is twice as flexible as the shaft 130, is met, the synthetic resin used may be the same or different. The shaft 130 and the ETB portion 130e are then connected using an appropriate method, for example, using the metal pipe as shown in FIG. 44. Note that in this arrangement, a mesh tube 130b is not enclosed in the shaft 130.

As a particular example, the ETB portion 130e may be made from soft polyvinyl chloride, polyethylene resin, polyurethane resin, silicon resin or the like, and the shaft 130 may be made from hard polyimide resin, HDPE, nylon resin, Teflon resin or the like.

Of course, as in previous embodiments, projected portion 11c on the forceps cups 11b may be arranged in a variety of ways. Further, the treating device 11 may be chosen according to the particular treatment required.

Figure 46:
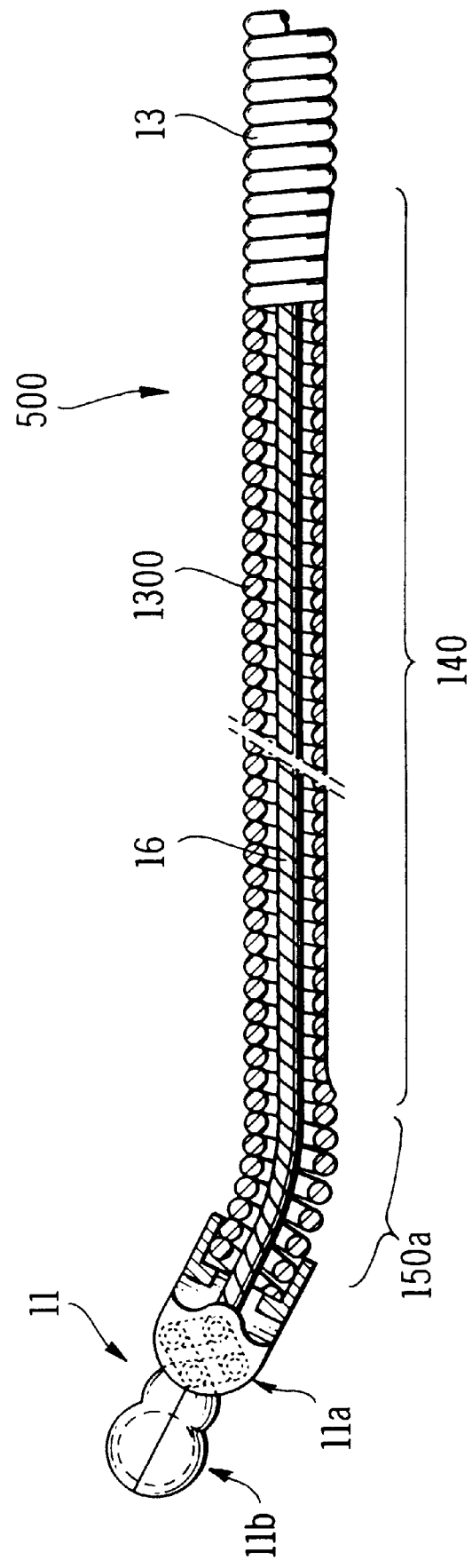
FIG. 46 is a sectional side view of a distal end of a treatment accessory according to a sixth embodiment of the invention.

FIG. 46 shows a distal end of a treatment accessory 500 according to a sixth embodiment of the invention. The treatment accessory 500 is similar to the above embodiments and includes the flexible shaft 13 formed as a wire coil and the treating device 11 (for example, forceps).

However, in this embodiment, the distal end portion of the flexible shaft 13 is formed to provide a directive bending portion 140 and a bent portion 150 between the directive bending portion 140 and the treating device 11.

Figure 48:
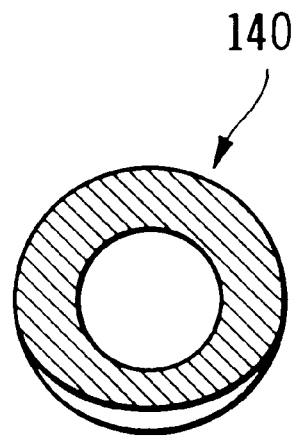
FIG. 48 is a sectional end view of a shaft of the treatment accessory of FIG. 46.
Figure 49:
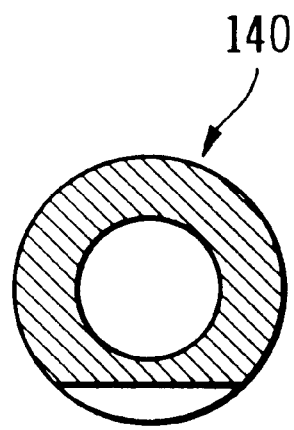
FIG. 49 is a sectional end view of an alternative arrangement of a shaft of the treatment accessory of FIG. 46.

As an example, the overall length of the flexible shaft 13 is 30–200 cm, the length of the directive bending portion 140 is 5–20 cm, and the length of the bent portion 150 is 1–5 cm The directive bending portion 140 is formed on the flexible shaft 13 by arranging the stainless steel coil 1300 that forms the flexible shaft 13 such that the thickness of the coil 1300 on one side of the flexible shaft 13 is thinner than on the other, that is, the side of the flexible shaft 13 has a decreased radius, as in FIG. 48, or is flattened, as in FIG. 49. As an example, a portion of the side of the flexible shaft 13 may be cut away using a grinder or the like to provide the flat surface shown in FIG. 49. The provision of the directive bending portion 140 makes the flexible shaft 13 easier to bend in the direction where the coil 1300 is thicker, i.e., the directive bending portion 140 is easier to bend in only one direction in a plane.

Figure 47:
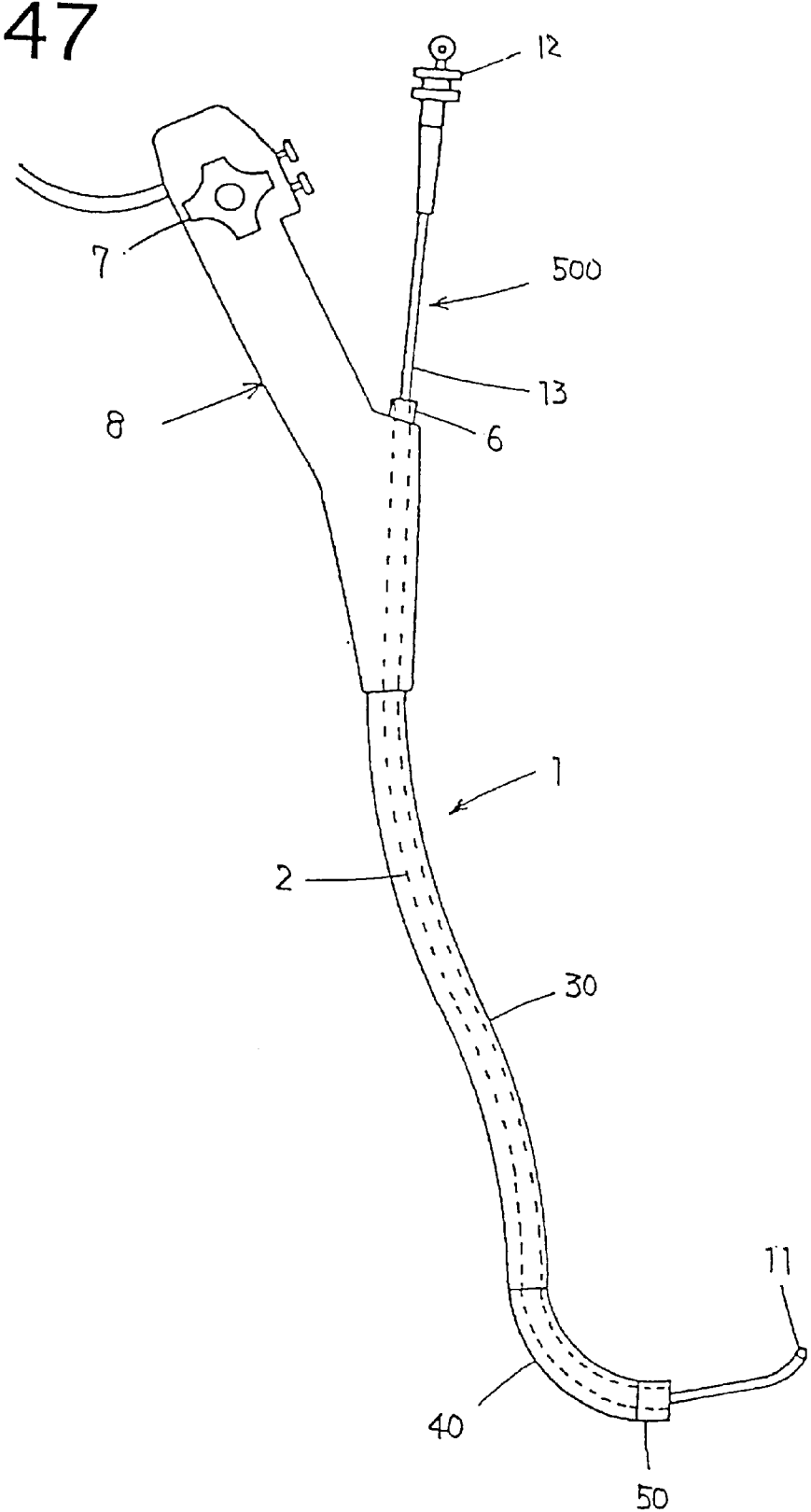
FIG. 47 is a side view of the endoscope having the forceps channel in which the treatment accessory of FIG. 46 is inserted.

As shown in FIG. 47, the endoscope 1 generally includes a bendable portion 40 that, during operation of the endoscope 1, may be bent as shown in FIG. 47. Thus, a portion of the treatment accessory 500 inside the bendable portion 40 of the endoscope 1 is bent accordingly.

In this embodiment, when the treatment accessory 500 is inserted in the forceps channel 2 as shown in FIG. 47, the directive bending portion 140 is located at the bendable portion 40. Thus, when the bendable portion 40 is bent, since the directive bending portion 140 bends in only one direction, the treatment accessory 500 will rotate inside the forceps channel 2 such that the directive bending portion 140 bends on the side where the coil 100 is thicker.

Accordingly, regardless of the initial orientation of the treatment accessory 500 inside the forceps channel 2, since the directive bending portion 140 is located at or passes through the bendable portion 40, the orientation of the treatment accessory 500 is adjusted accordingly.

With the above described structure, the directive bending portion 140 will remain straight without the application of an external force. Accordingly, the part of the directive bending portion 140 that extends from the distal end portion 50 of the endoscope 1 is straight in a neutral state.

As described above and as shown in FIG. 46, the flexible shaft 13 is also provided with the bent portion 150 between the treatment device 11 and the directive bending portion 140. The bent portion 150 is arranged to have a tendency to bend in a predetermined direction with respect to a direction of the directive bending portion 140 and the flexible shaft 13 in a neutral state.

Accordingly, as shown in FIG. 47, the treatment device 11 is directed in a predetermined direction at a predetermined angle as the rotational position of the treatment accessory 500 is adjusted by adjusting the bending portion 40 of the endoscope 1.

Figure 50:
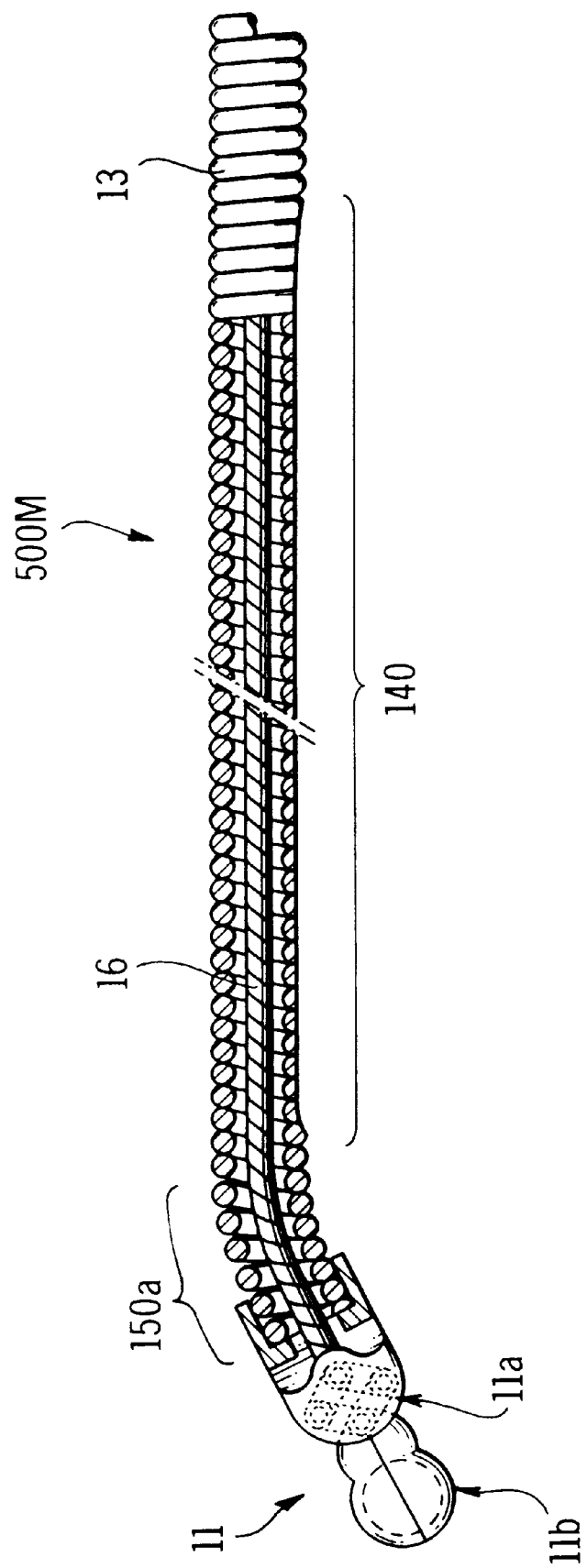
FIG. 50 is a sectional view of a distal end of a treatment accessory according to the sixth embodiment having an alternative structure.

The direction in which the bent portion 150 is bent is determined depending on the purpose of the treatment device 11, and is not limited to the direction shown in FIG. 46. An alternative arrangement is shown in FIG. 50. In this example, a bent portion 150a is bent in a direction opposite to the direction in which the directive bending portion 140 is easy to bend.

Figure 51:
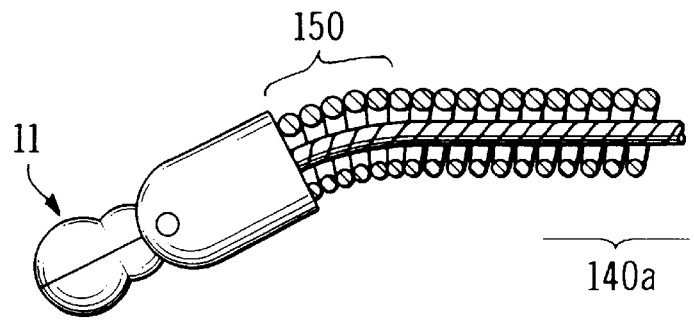
FIG. 51 is a sectional view of a distal end of a treatment accessory according to the sixth embodiment having another alternative structure.

Further, the structure of the directive bending portion 140 is also not limited to the example described above, and alternatives may be used. For example, as shown in FIG. 51, a directive bending portion 140a may be formed by varying the diameter of the wire forming the coil 1300 at opposite sides of the shaft 13. Further detail regarding the structure of such a coil 1300 is described in Japanese Patent Publication SHO 48-28751.

FIGS. 52 through 55 show applications of the treatment accessory 500 shown in FIG. 46, in which the bent portion 150 is bent in the direction in which the directive bending portion 140 is easy to bend.

Figure 52:
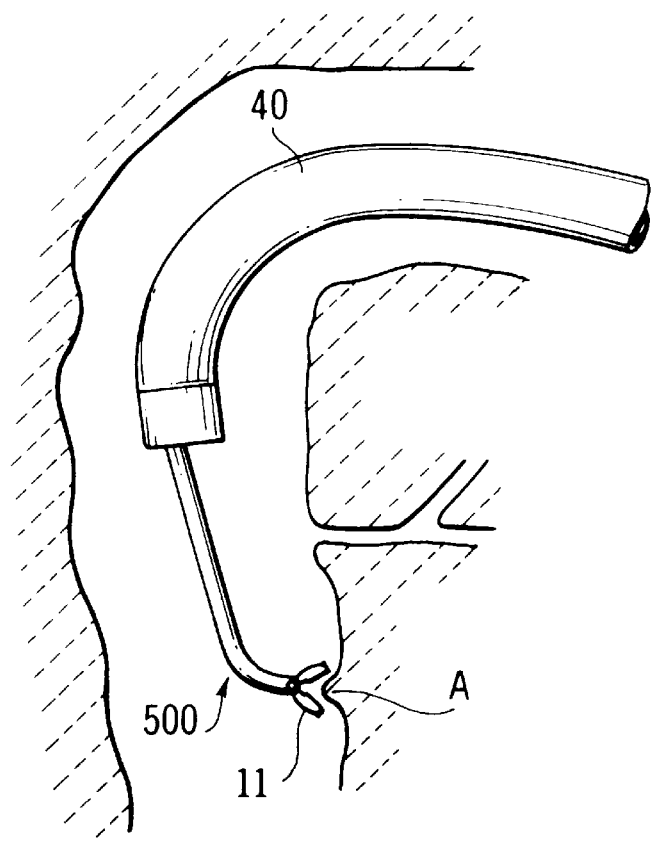
FIG. 52 is a schematic view illustrating the use of the treatment accessory shown in FIG. 46 in a duodenum.

In FIG. 52, a biopsy forceps is used as the treating device 11 and an affected part A in a duodenum is treated.

Figure 53:
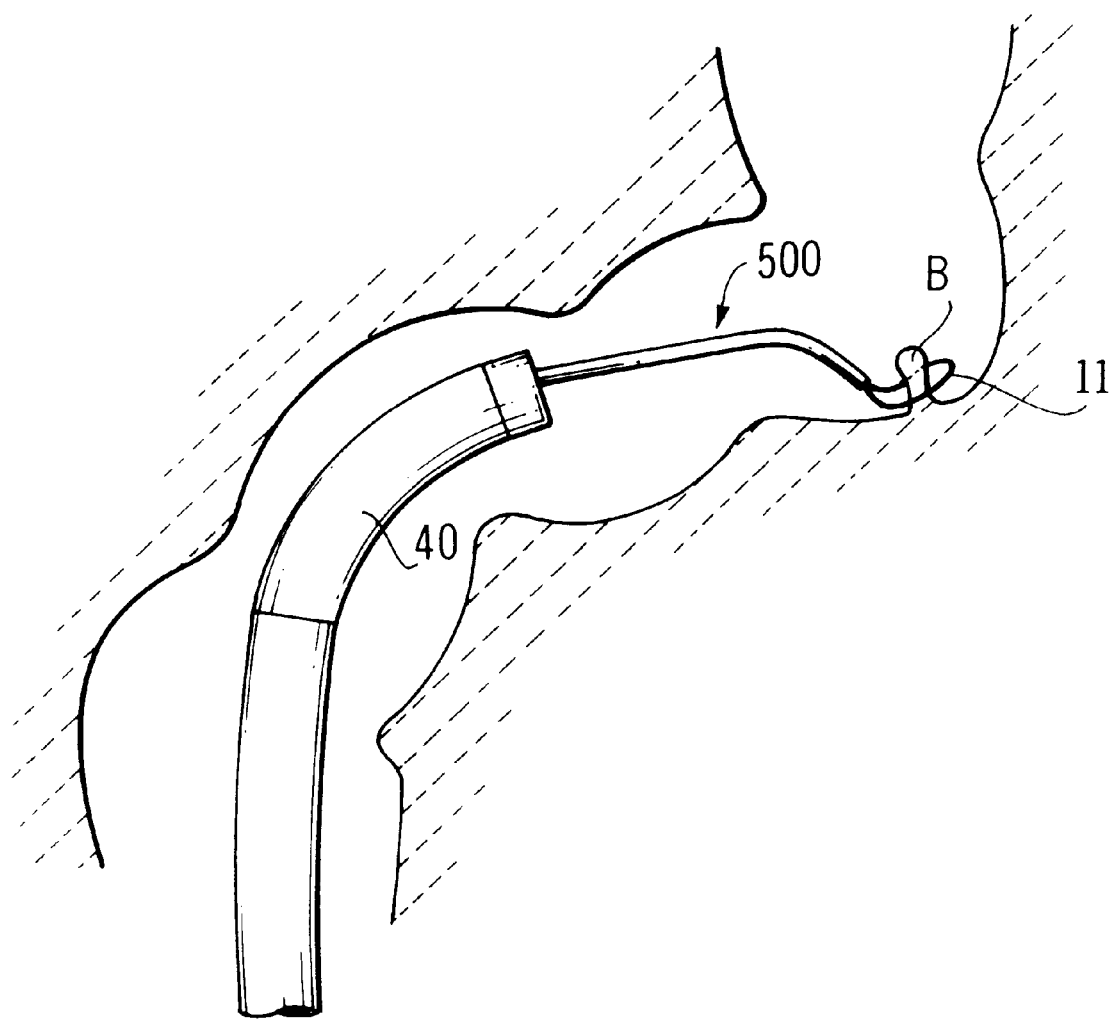
FIG. 53 is a schematic view illustrating the use of the treatment accessory shown in FIG. 46 in a colon.

In FIG. 53, a high-frequency snare is used as the treating device 11 and an affected part B in a colon is treated.

Figure 54:
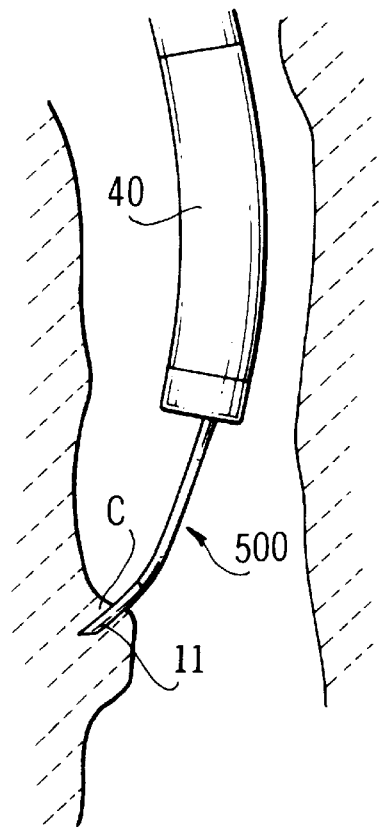
FIG. 54 is a schematic view illustrating the use of the treatment accessory shown in FIG. 46 in an esophagus.

In FIG. 54, an injector is used as the treating device 11 and an affected part C in an esophagus is treated.

Figure 55:
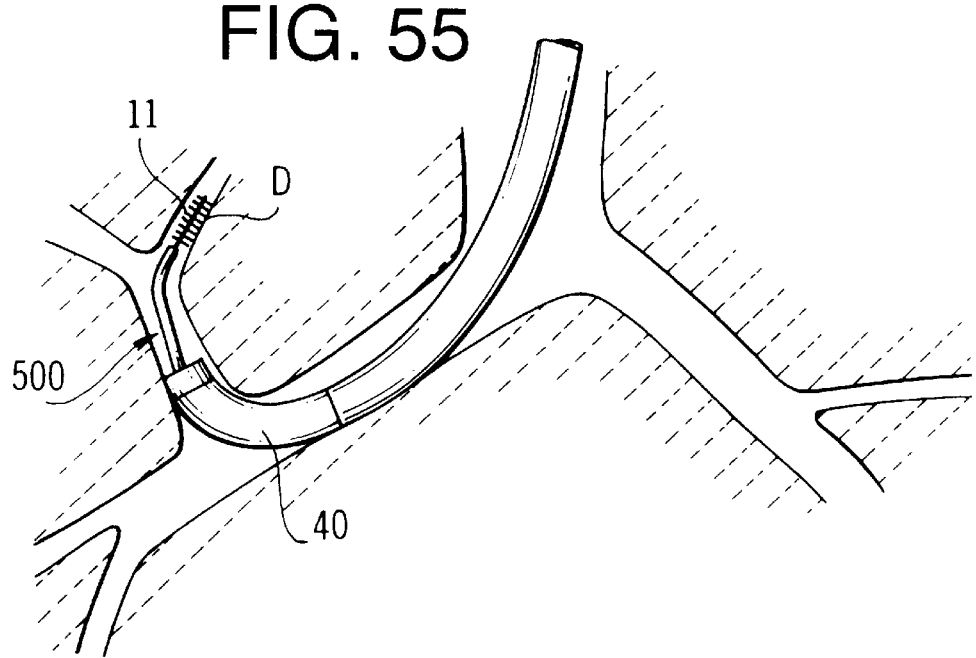
FIG. 55 is a schematic view illustrating the use of the treatment accessory shown in FIG. 46 in a bronchial tube.

In FIG. 55, a cytology brush is used as the treating device 11 and an affected part D in a bronchial tube is treated.

FIGS. 56 through 59 show applications of the treatment accessory 500M shown in FIG. 50, in which the bent portion 150a is bent in an opposite direction to the direction in which the directive bending portion 140 is easy to bend.

Figure 56:
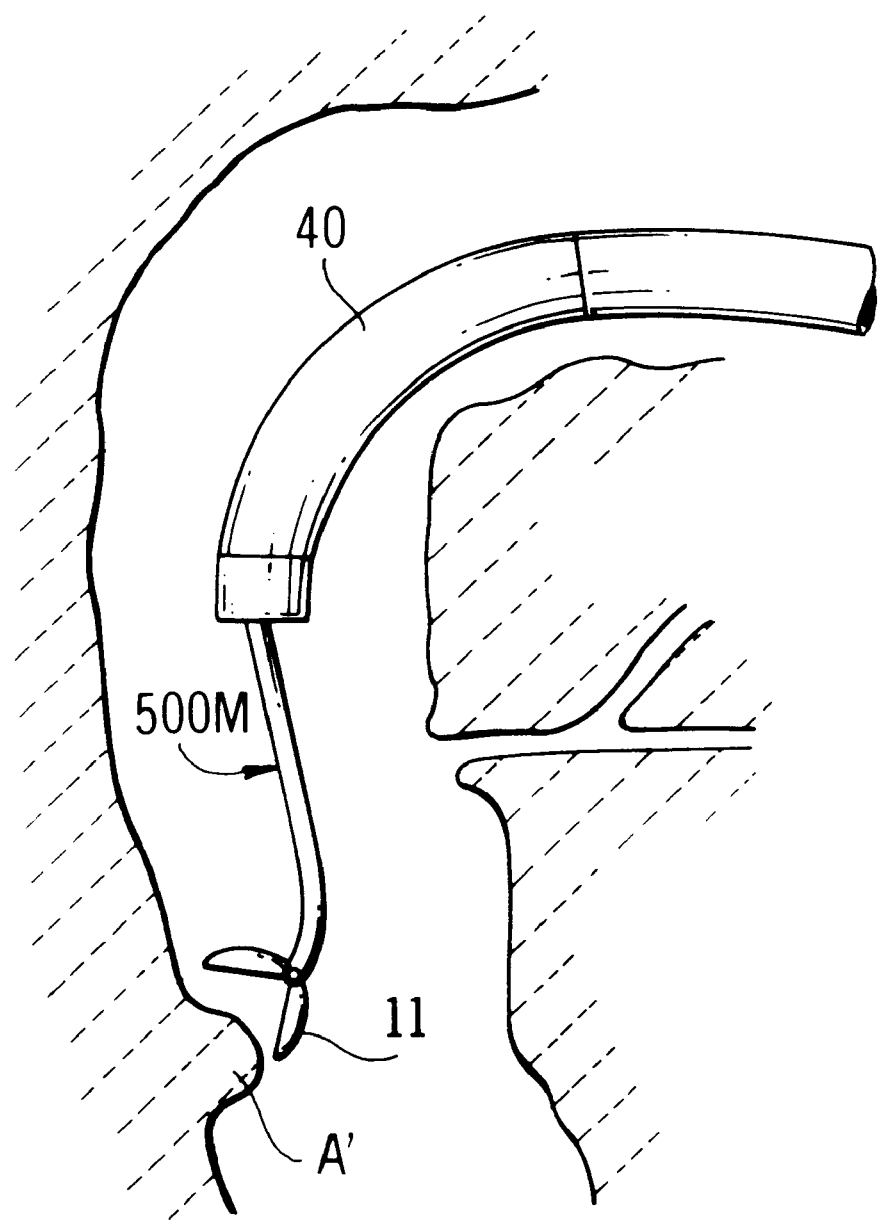
FIG. 56 is a schematic view illustrating the use of the treatment accessory shown in FIG. 50 in a duodenum.
Figure 57:
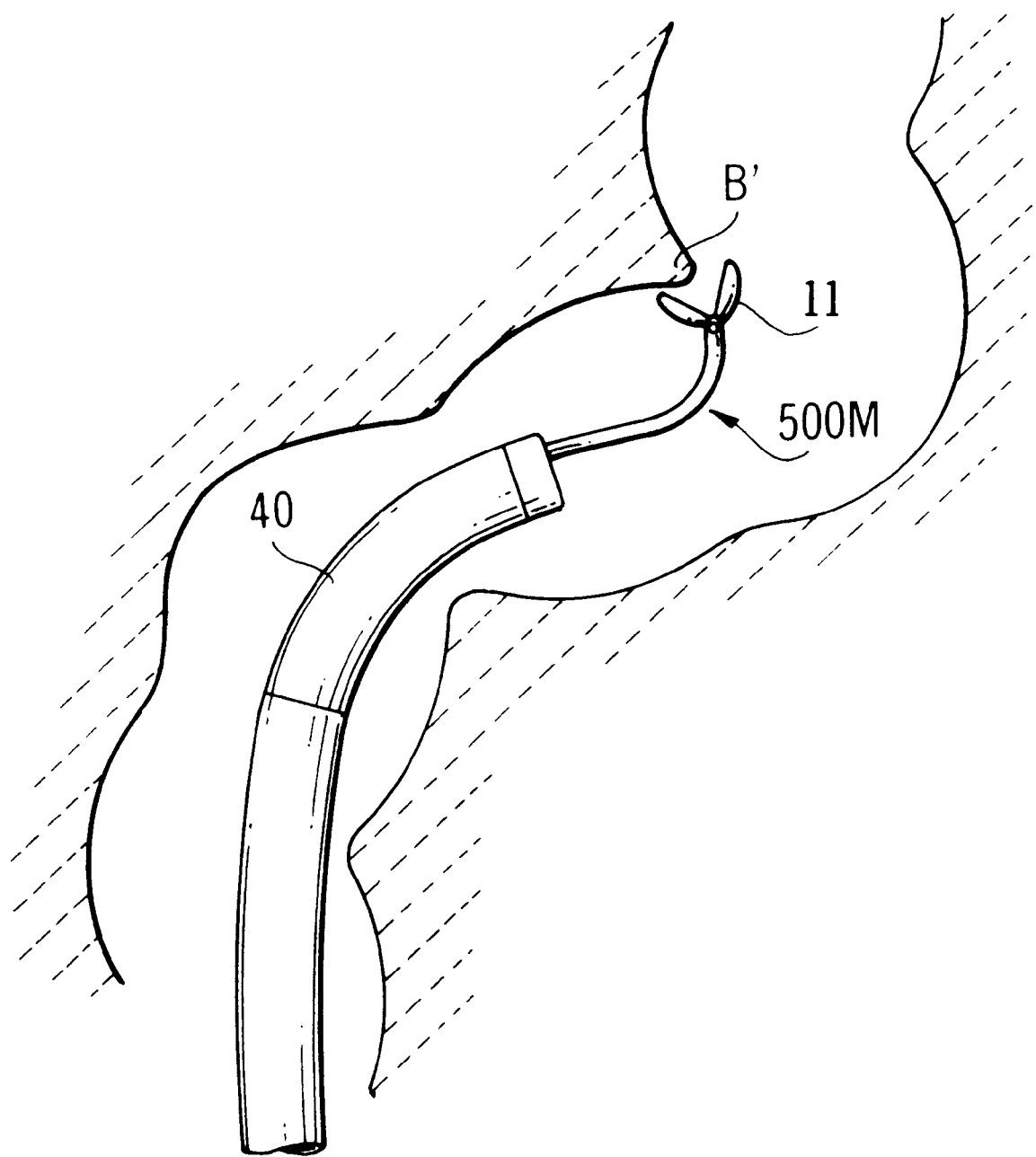
FIG. 57 is a schematic view illustrating the use of the treatment accessory shown in FIG. 50 in a colon.

In FIG. 56, biopsy forceps are used as the treating device 11 and an affected part A' in a duodenum is treated In FIG. 57, again using biopsy forceps, an affected part B' in a colon is treated.

Figure 58:
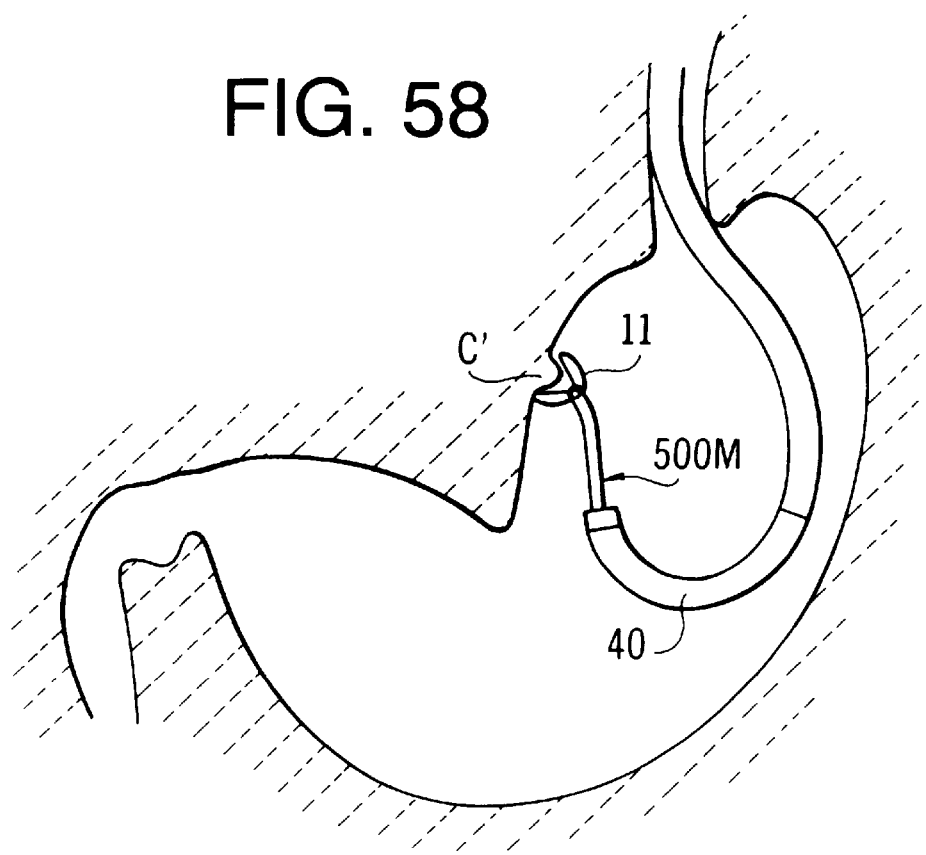
FIG. 58 is a schematic view illustrating the use of the treatment accessory shown in FIG. 50 in an esophagus.

In FIG. 58, also using biopsy forceps, an affected part C' in an esophagus is treated.

Figure 59:
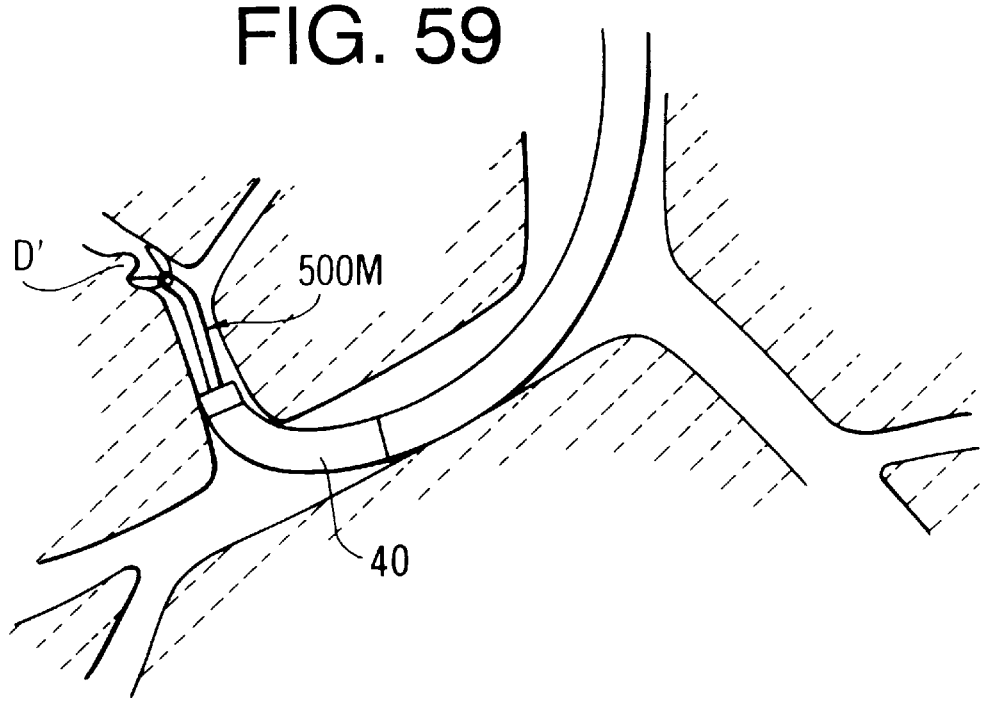
FIG. 59 is a schematic view illustrating the use of the treatment accessory shown in FIG. 50 in a bronchial tube.

In FIG. 59, the biopsy forceps are used to treat an affected part D' in a bronchial tube.

Using the arrangement of the sixth embodiment, by adjusting the directive bending portion 140 and the bent portion 150 accordingly in accordance with the particular operation required of the treatment accessory 500, the direction and angle of the treating device 11 can be set such that the treating device 11 can be inserted into small areas such as the branch of a bronchial tube and such that the treating device 11 comes into appropriate contact with the affected part (i.e., contacts the affected part from the "front" thereof).

Figure 60:
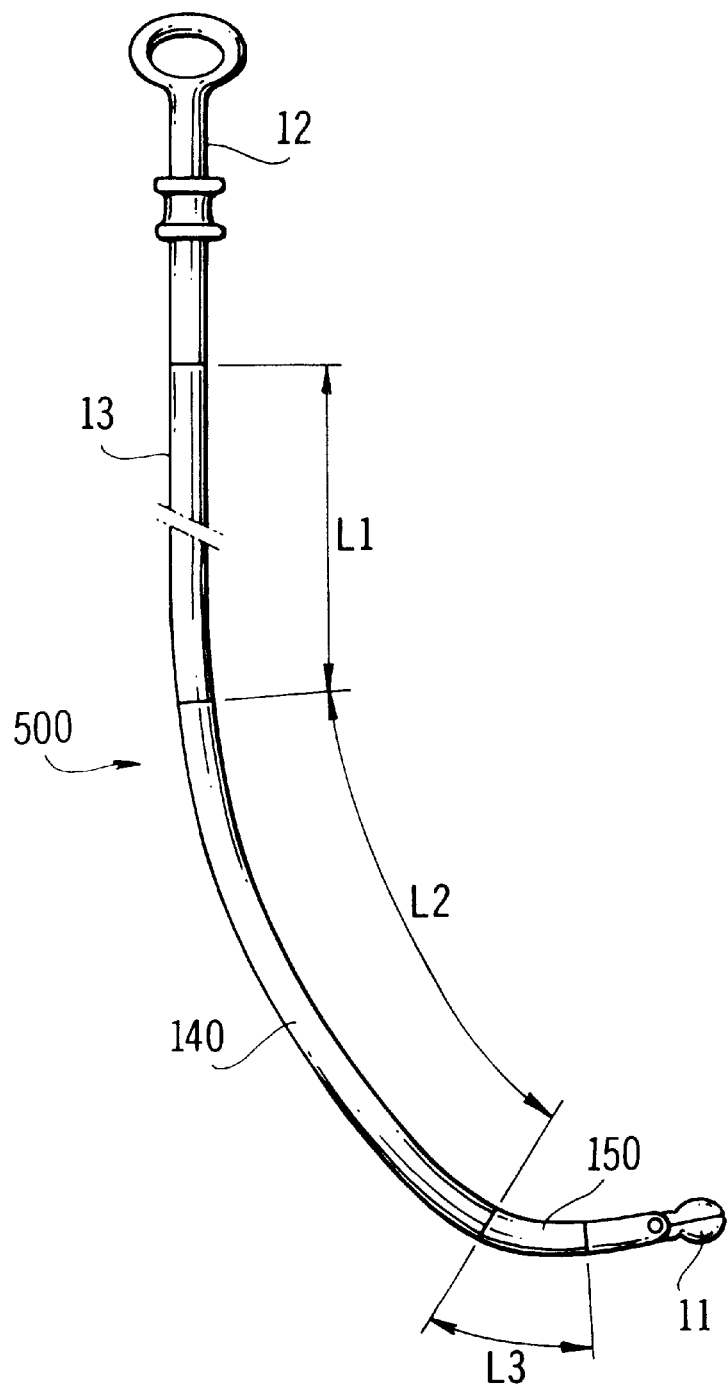
FIG. 60 is a side view of the treatment accessory of FIG. 46 illustrating the lengths of related elements.

As shown in FIG. 60, the length of each portion of the treatment accessory 500 is preferably within the following ranges: the length L1 of the flexible shaft 13 is 30–200 cm; the length L2 of the directive bending portion 140 is 5–20 cm; and the length L3 of the bent portion 150 is 1–5 cm.

Although the structure and operation of treatment accessories for an endoscope are described herein with respect to the preferred embodiments, many modifications and changes can be made without departing from the spirit and scope of the invention.

The present disclosure relates to subject matters contained in Japanese Patent Application No. HEI 07-130195, filed on May 29, 1995, No. HEI 07-140148, filed on Jun. 7, 1995, No. HEI 07-141478, filed on Jun. 8, 1995, No. HEI 07-146978, filed on Jun. 14, 1995, No. HEI 07-174546, filed on Jul. 11, 1995, No. HEI 08-267186, filed on Oct. 8, 1996, No. HEI 09-3440, filed on Jan. 13, 1997, No. HEI 09-22268, filed on Feb. 5, 1997, which are expressly incorporated herein by reference in their entirety.

What is claimed is:

1. A treatment apparatus for use with an endoscope, said treatment apparatus being inserted in a forceps channel of said endoscope, said treatment apparatus comprising:

a treatment instrument;

an elongated flexible element connected to said treatment instrument at a distal end of said flexible element, said flexible element including at least two bendable portions, a first bendable portion having a predetermined flexibility, a second bendable portion having a greater flexibility and being shorter than said first bendable portion, said second bendable portion being located between said first bendable portion and said treatment instrument, said second bendable portion including a plurality of pivotally connected annular pipe portions, at least a portion of said first bendable portion and the entire second bendable portion protruding from a distal end of said forceps channel when said treatment instrument is in use.

2. The treatment apparatus according to claim 1, wherein said second bendable portion is more flexible than said first bendable portion in one direction.

3. The treatment apparatus according to claim 2, wherein said treatment instrument is a forceps having jaws which open in a predetermined direction, said one direction being said predetermined direction.

4. The treatment apparatus according to claim 2, wherein said treatment instrument is a forceps having jaws which open in a predetermined direction, said one direction being perpendicular to said predetermined direction.

5. The treatment apparatus according to claim 1, wherein the second bendable portion is bendable in any direction.

6. The treatment apparatus according to claim 1, wherein said second bendable portion comprises a flexible cylindrical member having cut-out portions.

7. The treatment apparatus according to claim 1, wherein the bending angle of said second bendable portion is less than 70 degrees.

8. The treatment apparatus according to claim 1, wherein the length of said second bendable portion is equal to or less than 50 mm.

9. A treatment apparatus for use with an endoscope, said treatment apparatus being inserted in a forceps channel of said endoscope, said treatment apparatus comprising:

a treatment instrument;

an elongated flexible element connected to said treatment instrument at a distal end of said flexible element, said flexible element including at least two bendable portions, a first bendable portion having a predetermined flexibility, a second bendable portion having a greater flexibility and being shorter than said first bendable portion, said second bendable portion being located between said first bendable portion and said treatment instrument, at least a portion of said first bendable portion and the entire second bendable portion protruding from a distal end of said forceps channel when said treatment instrument is in use, wherein said second bendable portion comprises a metal coil embedded between inner and outer surfaces of a cylindrical elastic material.

10. A treatment apparatus for use with an endoscope, said treatment apparatus being inserted in a forceps channel of said endoscope, said treatment apparatus comprising:

a treatment instrument;

an elongated flexible element connected to said treatment instrument at a distal end of said flexible element, said flexible element including at least two bendable portions, a first bendable portion having a predetermined flexibility, a second bendable portion having a greater flexibility and being shorter than said first bendable portion, said second bendable portion being located between said first bendable portion and said treatment instrument, at least a portion of said first bendable portion and the entire second bendable portion protruding from a distal end of said forceps channel when said treatment instrument is in use, wherein said first and second bendable portions comprise wound coils, the coils of the second bendable portion being more loosely wound than said first bendable portion.

11. A treatment apparatus for use with an endoscope, said treatment apparatus being inserted in a forceps channel of said endoscope, said treatment apparatus comprising:

a treatment instrument;

an elongated flexible element connected to said treatment instrument at a distal end of said flexible element, said flexible element including at least two bendable portions, a first bendable portion having a predetermined flexibility, a second bendable portion having a greater flexibility and being shorter than said first bendable portion, said second bendable portion being located between said first bendable portion and said treatment instrument, at least a portion of said first bendable portion and the entire second bendable portion protruding from a distal end of said forceps channel when said treatment instrument is in use, wherein said first and second bendable portions comprise flexible sheaths, and a mesh material being embedded in only said first bendable portion.

12. A treatment apparatus for use with an endoscope, said treatment apparatus being inserted in a forceps channel of said endoscope, said treatment apparatus comprising:

a treatment instrument;

an elongated flexible element connected to said treatment instrument at a distal end of said flexible element, said flexible element including at least two bendable portions, a first bendable portion having a predetermined flexibility, a second bendable portion having a greater flexibility and being shorter than said first bendable portion, said second bendable portion being located between said first bendable portion and said treatment instrument, at least a portion of said first bendable portion and the entire second bendable portion protruding from a distal end of said forceps channel when said treatment instrument is in use, wherein said first and second bendable portions are formed of different materials.

13. A treatment apparatus for use with an endoscope, said endoscope having a bendable portion at a distal end, said treatment apparatus being inserted in a forceps channel of said endoscope, said treatment apparatus comprising:

a treatment instrument;

an elongated flexible element connected to said treatment instrument at a distal end of said flexible element, said flexible element including at least two bendable portions, a first bendable portion having a predetermined flexibility, a second bendable portion being more flexible in one direction than said first bendable portion, said second bendable portion being located between said first bendable portion and said treatment instrument and being located at the bendable portion of said endoscope when inserted in said forceps channel, said first and second bendable portions including wound coils, the coils of the second bendable portion being thinner than the coils of said first bendable portion.

14. A treatment apparatus for use with an endoscope, said treatment apparatus being inserted in a forceps channel of said endoscope, said treatment apparatus comprising:

a treatment instrument for treating an object to be treated, said treatment instrument having grasping jaws, each grasping jaw having a tip at a distal end, at least one projection being provided on each of said grasping jaws, said at least one projection being laterally spaced from a respective tip of each said grasping jaw; and an elongated flexible element connected to said treatment instrument at a distal end of said flexible element, said elongated flexible element including a first bendable portion having a predetermined flexibility, a second bendable portion having a greater flexibility than said first bendable portion, said second bendable portion being located between said first bendable portion and said treatment instrument, whereby when said at least one projection contacts said object to be treated, said second bendable portion bends to position said treatment instrument with respect to said object to be treated.

15. The treatment apparatus according to claim 14, wherein said jaws contact each other at a contact portion when closed, each of said projections being spaced from said contact portion.

16. The treatment apparatus according to claim 14, wherein each of said projections is half-ring shaped.

17. The treatment apparatus according to claim 14, wherein each of said projections is cone-shaped.

18. The treatment apparatus according to claim 14, comprising a plurality of projections on each of said jaws.

19. A treatment apparatus for use with an endoscope, said treatment apparatus being inserted in a forceps channel of said endoscope, said treatment apparatus comprising:

a treatment instrument for treating an object to be treated, said treatment instrument having grasping jaws, and at least one projection being provided on each of said grasping jaws such that said projection does not extend beyond a plane perpendicular to a distal end of said grasping jaws; and an elongated flexible element connected to said treatment instrument at a distal end of said flexible element, whereby when said at least one projection contacts said object to be treated, said flexible element bends to position said treatment instrument with respect to said object to be treated.

20. A treatment apparatus for use with an endoscope, said treatment apparatus being inserted in a forceps channel of said endoscope, said treatment apparatus comprising:

a treatment instrument;

an elongated flexible element connected to said treatment instrument at a distal end of said flexible element, said flexible element including at least two bendable portions, a first bendable portion having a predetermined flexibility, a second bendable portion having a greater flexibility and being shorter than said first bendable portion, said second bendable portion being located between said first bendable portion and said treatment instrument, said second bendable portion being bendable within only one plane, at least a portion of said first bendable portion and the entire second bendable portion protruding from a distal end of said forceps channel when said treatment instrument is in use.

21. The treatment apparatus according to claim 20, further comprising a third bendable portion located between said second bendable portion and said treatment instrument, said third bendable portion being bent at a predetermined angle with respect to said second bendable portion.

22. The treatment apparatus according to claim 21, wherein said third bendable portion is bent in the same direction as said one direction of said second bendable portion.

23. The treatment apparatus according to claim 21, wherein said third bendable portion is bent in the opposite direction as said one direction of said second bendable portion.

24. The treatment apparatus according to claim 20, wherein said second bendable portion comprises wound coils, each coil having a first large diameter portion and a second opposed portion being smaller than said first large diameter portion.

25. A treatment apparatus for use with an endoscope, said treatment apparatus being inserted in a forceps channel of said endoscope, said treatment apparatus comprising:

a treatment instrument;

an elongated flexible element connected to said treatment instrument at a distal end of said flexible element, said flexible element including at least two bendable portions, a first bendable portion having a predetermined flexibility, a second bendable portion having a greater flexibility and being shorter than said first bendable portion, said second bendable portion being located between said first bendable portion and said treatment instrument, at least a portion of said first bendable portion and the entire second bendable portion protruding from a distal end of said forceps channel when said treatment instrument is in use, said first and second bendable portions including wound coils, the coil diameter of said second bendable portion being smaller than the coil diameter of said first bendable portion.

26. A treatment apparatus for use with an endoscope, said treatment apparatus being inserted in a forceps channel of said endoscope, said treatment apparatus comprising:

a treatment instrument;

an elongated flexible element connected to said treatment instrument at a distal end of said flexible element, said flexible element including at least two bendable portions, a first bendable portion including a mesh tube to provide a predetermined flexibility, a second bendable portion having a greater flexibility and being shorter than said first bendable portion, said second bendable portion being located between said first bendable portion and said treatment instrument, at least a portion of said first bendable portion and the entire second bendable portion protruding from a distal end of said forceps channel when said treatment instrument is in use.

27. A treatment apparatus for use with an endoscope, said treatment apparatus being inserted in a forceps channel of said endoscope, said treatment apparatus comprising:

a treatment instrument;

an elongated flexible element connected to said treatment instrument at a distal end of said flexible element, said flexible element including at least two bendable portions, a first bendable portion having a predetermined flexibility, a second bendable portion being formed separately from said first bendable portion and having a greater flexibility and being shorter than said first bendable portion, said second bendable portion being located between said first bendable portion and said treatment instrument, at least a portion of said first bendable portion and the entire second bendable portion protruding from a distal end of said forceps channel when said treatment instrument is in use.

28. A treatment apparatus for use with an endoscope, said treatment apparatus being inserted in a forceps channel of said endoscope, said treatment apparatus comprising:

a treatment instrument;

an elongated flexible element connected to said treatment instrument at a distal end of said flexible element, said flexible element including at least two bendable portions, a first bendable portion having a predetermined flexibility, a second bendable portion being formed from a coil and having a greater flexibility and being shorter than said first bendable portion, said second bendable portion being located between said first bendable portion and said treatment instrument and being connected to said first bendable portion by a metal pipe, at least a portion of said first bendable portion and the entire second bendable portion protruding from a distal end of said forceps channel when said treatment instrument is in use.

* * * * *

UNITED STATES PATENT AND TRADEMARK OFFICE
CERTIFICATE OF CORRECTION

PATENT NO. : 5,904,647
DATED : May 18, 1999
INVENTOR(S) : T. OUCHI

It is certified that error appears in the above-indentified patent and that said Letters Patent is hereby corrected as shown below:

On the cover page of the printed patent, at item [73], Assignee, after "Asahi" insert ---Kogaku---.

Signed and Sealed this

Second Day of May, 2000

Attest:

Q. TODD DICKINSON

Attesting Officer     Director of Patents and Trademarks